(12) United States Patent
Hatanaka et al.

(10) Patent No.: US 10,377,795 B2
(45) Date of Patent: Aug. 13, 2019

(54) RARE EARTH MATERIAL-BINDING PEPTIDE AND USE THEREOF

(71) Applicant: KABUSHIKI KAISHA TOYOTA CHUO KENKYUSHO, Nagakute-shi, Aichi-ken (JP)

(72) Inventors: Takaaki Hatanaka, Nagakute (JP); Nobuhiro Ishida, Nagakute (JP)

(73) Assignee: KABUSHIKI KAISHA TOYOTA CHUO KENKYUSHO, Nagakute-shi (JP)

( * ) Notice: Subject to any disclaimer, the term of this patent is extended or adjusted under 35 U.S.C. 154(b) by 0 days.

(21) Appl. No.: 15/113,287

(22) PCT Filed: Jan. 21, 2015

(86) PCT No.: PCT/JP2015/000270
§ 371 (c)(1),
(2) Date: Jul. 21, 2016

(87) PCT Pub. No.: WO2015/111407
PCT Pub. Date: Jul. 30, 2015

(65) Prior Publication Data
US 2017/0008926 A1 Jan. 12, 2017

(30) Foreign Application Priority Data
Jan. 22, 2014 (JP) .................................. 2014-009848

(51) Int. Cl.
*A61K 51/00* (2006.01)
*A61K 36/14* (2006.01)
*C07K 7/06* (2006.01)
*C01F 17/00* (2006.01)
*C07K 7/08* (2006.01)
*C22B 59/00* (2006.01)
*G01N 33/68* (2006.01)
*G01N 33/84* (2006.01)

(52) U.S. Cl.
CPC ............... *C07K 7/06* (2013.01); *C01F 17/00* (2013.01); *C07K 7/08* (2013.01); *C22B 59/00* (2013.01); *G01N 33/6803* (2013.01); *G01N 33/84* (2013.01)

(58) Field of Classification Search
CPC ............ A61K 38/00; A61K 2123/00; A61K 2121/00; A61K 49/0004; A61K 49/0008; A61K 38/03; A61K 38/04; A61K 38/02; A61K 49/00; A61K 51/00; C07K 7/06; C07K 7/08; C01F 17/00; C22B 59/00; G01N 33/6803; G01N 33/84
USPC ..... 424/1.11, 1.69, 9.1, 9.2; 530/300; 514/1, 514/1.1
See application file for complete search history.

(56) References Cited

U.S. PATENT DOCUMENTS

2003/0228622 A1 12/2003 Imperiali et al.
2012/0219504 A1 8/2012 Cho et al.

FOREIGN PATENT DOCUMENTS

| JP | 2007-523890 A | 8/2007 |
| JP | 2012-193155 A | 10/2012 |
| JP | 2013-509452 A | 3/2013 |
| JP | 2014-051449 A | 3/2014 |
| WO | 03/027122 A2 | 4/2003 |
| WO | 2005/101993 A2 | 11/2005 |

OTHER PUBLICATIONS

Chiu, Chin-Yi et al; Platinum nanocrystals selectively shaped using facet-specific peptide sequences; Nature Chemistry; vol. 3, pp. 393-399; 2011.
Meyers, Steven R. et al.; Endothelialization of Titanium Surfaces; Advanced Materials; vol. 19; pp. 2492-2498; 2007.
Nitz, Mark et al; Structural Origin of the High Affinity of a Chemically Evolved Lanthanide-Binding Peptide; Angew. Chem. Int. Ed; pp. 3682-3685; vol. 43; 2004.
Lim S. et al; Visions & Reflections; Lanthanide-binding peptides and the enzymes that Might Have Been; CMLS, Cellular and Molecular Life Sciences; vol. 61; No. 17; Aug. 2004.
Bonnet, C'elia S. et al; Luminescent lanthanide-binding peptides: sensitising the excited states of Eu(III) and Tb(III) wiith a 1,8-naphthalimide-based antenna; Organic Biomolecular Chemistry; vol. 10; pp. 126-133; Jan. 1, 2012.
Claïnche, Le Loïc et al; Modulating the Affinity and the Selectivity of Engineered Calmodulin EF-Hand Peptides for Lanthanides; Biotechnology and Bioengineering; vol. 95; No. 1; pp. 29-36; Sep. 5, 2006.
Atkinson, Paul et al; A cationic lanthanide complex binds selectively to phosphorylated tyrosine sites, aiding NMR analysis of the phosphorylated insulin receptor peptide fragment; Organic & Biomlecular Chemistry; vol. 4; No. 16; pp. 3166-3171; Jan. 1, 2006.
Clark, Ian D. et al; A novel peptide designed for sensitization of terbium (III) luminescence; FEBS Letters; vol. 333; No. 1,2; pp. 96-98; Oct. 1993.
Sueda, Shinji et al; A luminescent affinity tag for proteins based on the terbium(III)-binding peptide; Analytical Biochemistry; vol. 422; No. 1; pp. 52-54; 2012.

(Continued)

*Primary Examiner* — D. L. Jones
(74) *Attorney, Agent, or Firm* — Oliff PLC

(57) ABSTRACT

A binding agent is capable of binding to rare earth materials such as rare earths and inorganic compounds thereof. A rare earth material-binding agent includes a peptide capable of binding to a rare earth material including a rare earth and a rare earth inorganic compound.

8 Claims, 11 Drawing Sheets
Specification includes a Sequence Listing.

(56) References Cited

OTHER PUBLICATIONS

Saio, Tomohide et al; Two-point anchoring of a lanthanide-binding peptide to a target protein enhances the paramagnetic anisotropic effect; Journal of Biomolecular NMR; vol. 44; No. 3; pp. 157-166; May 26, 2009.

Caravan, Peter et al; Gadolinium-binding helix-turn-helix-peptides; DNA-dependent MRI contrast agents; The Royal Society of Chemistry; No. 20; pp. 2574-2575; Oct. 21, 2003.

Nakatsukasa, Takako et al; Site-specific DNA cleavage by artificial zinc finger-type nuclease with cerium-binding peptide; Biochemical and Biophysical Research Communications; vol. 330; No. 1; pp. 247-252; Apr. 29, 2005.

Nitz, Mark et al; A Powerful Combinatorial Screen to Identify High-Affinity Terbium(III)-Binding Peptides; Chembiochem; A European Journal of Chemical Biology; vol. 4; No. 4; pp. 272-276; Apr. 4, 2003.

Kupke, Donald W. et al; Volume Changes in the Binding of Lanthanides to Peptide Analogues of Loop II of Calmodulin; Biochemistry; vol. 28; No. 10; pp. 4409-4415; May 1, 1989.

Bondon, Arnaud et al; A possible calcium binding site in animal lectins: a sup1H-NMR study of the interaction between lanthanides and a synthetic peptide from a highly conserved domain of Pleurodeles lectin; Biochimica et Biophysica Acta. Molecular Cell Research, Elsevier Science Publishers; vol. 1135; No. 1; pp. 19-26; Apr. 30, 1992.

Mackenzie, C. Roger et al; Bifunctional fusion proteins consisting of a single-chain antibody and an engineered anthanide-binding protein; Immunotechnology, Elsevier Science BV.; vol. 1; No. 2; pp. 139-150; Aug. 1, 1995.

Kremer, Carlos et al; Structure and thermodynamic stability of lanthanide complexes with amino acids and peptides; Coordiniation Chemistry Reviews, Elvsevier Science; vol. 249; No. 5-6; pp. 567-590; Mar. 1, 2005.

Zhuang, Tiandi et al; Structure determination of a Galectin-3-carbohydrate complex using paramagnetism-based NMR constraints; Proetin Science; vol. 17; No. 7; pp. 1220-1231; Jul. 1, 2008.

Su, Xun-Cheng et al; Site-Specific Labelling of Proteins with a Rigid Lanthanide-Binding Tag; ChemBioChem; vol. 7; No. 10; pp. 1599-1604; Oct. 6, 2006.

Bernardi, Francesca et al; Solution Structures of Cyclosporin A and Its Complex with Dysprosium(III) in SDS Micelles: NMR and Molecular Dynamics Studies; Journal of Physical Chemistry B.; vol. 112; No. 3; pp. 828-835; 2008.

Aug. 4, 2015 Search Report issued in International Patent Application No. PCT/JP2015/000270.

Aug. 4, 2015 Written Opinion of the International Searching Authority issued in International Patent Application No. PCT/JP2015/000270.

Takenori Ishida, "Mukizairyou-ketsugou-peptide de tsukuru Nanomaterial," Biodmedia, 2012, vol. 1, p. 37.

Sep. 18, 2018 Office Action issued in Japanese Application No. 2016-547966.

Feb. 3, 2019 Office Action issued in Chinese Application No. 201580005629.8.

[Fig.1]
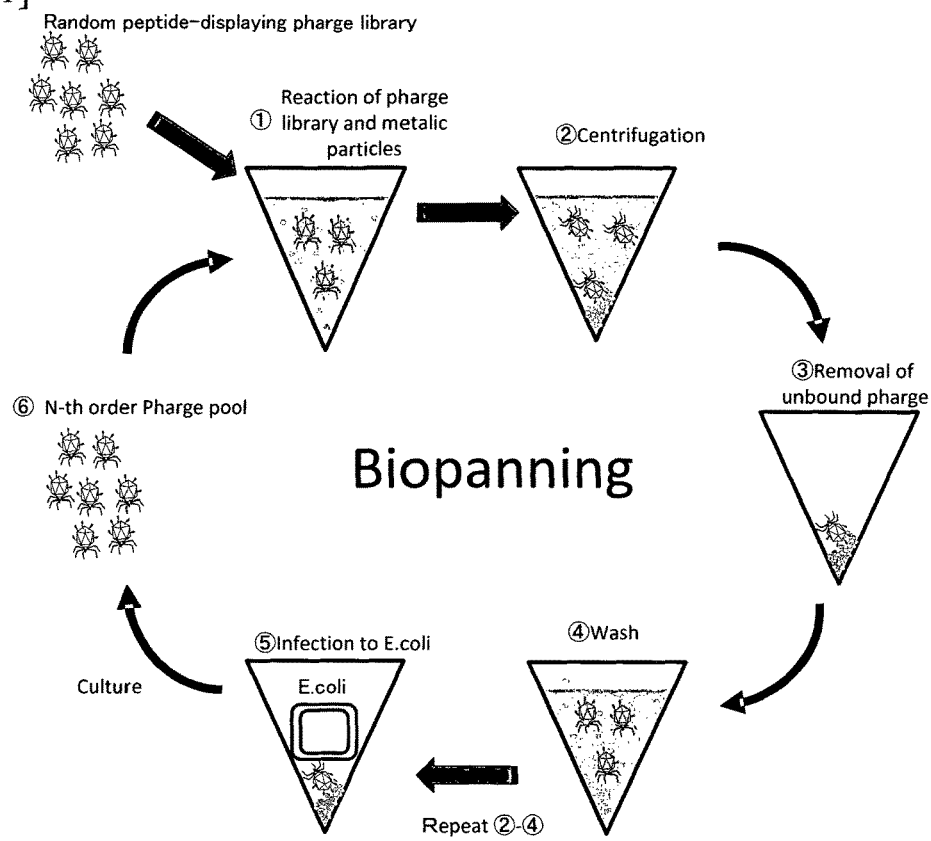
[Fig.2]
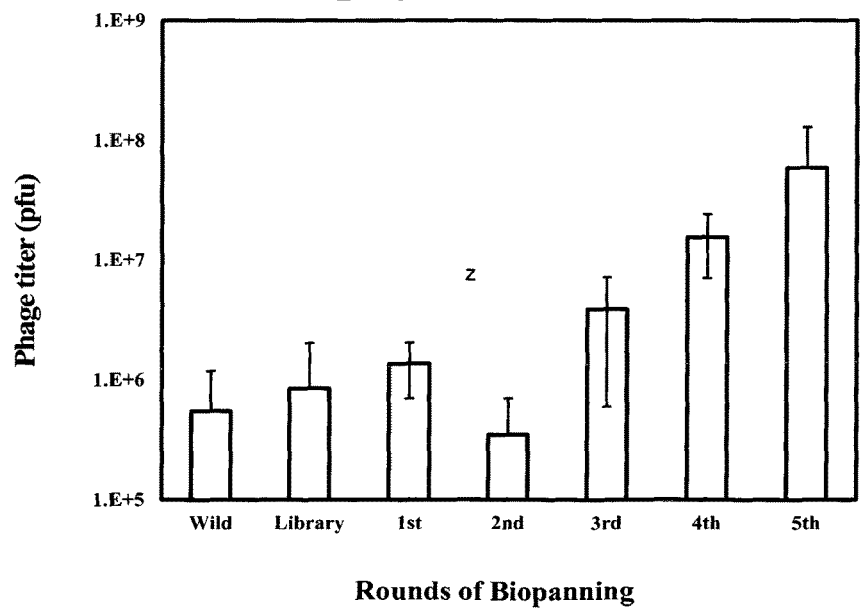

[Fig. 3]
Evaluation of the ability of monoclonal pharge binding to Dy$_2$O$_3$
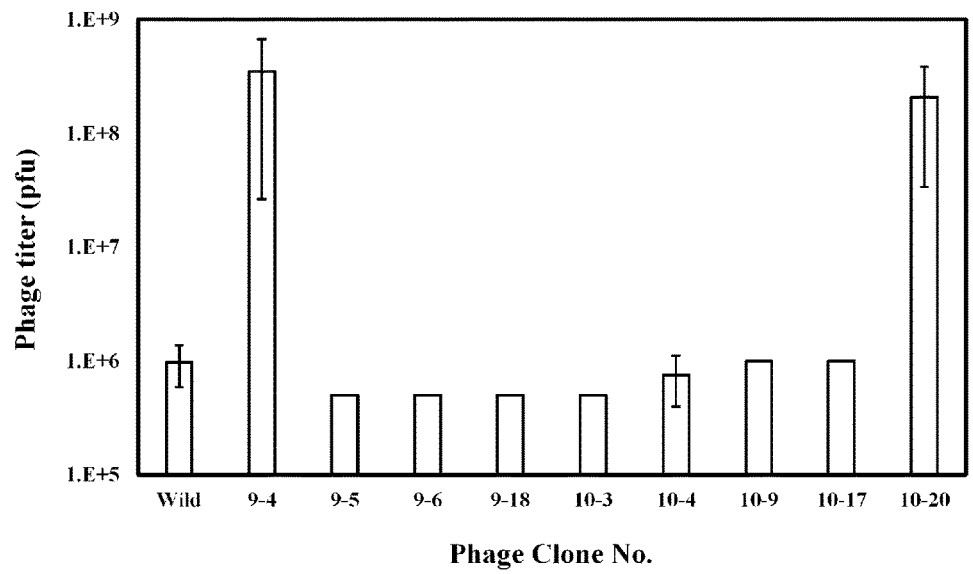
[Fig. 4]
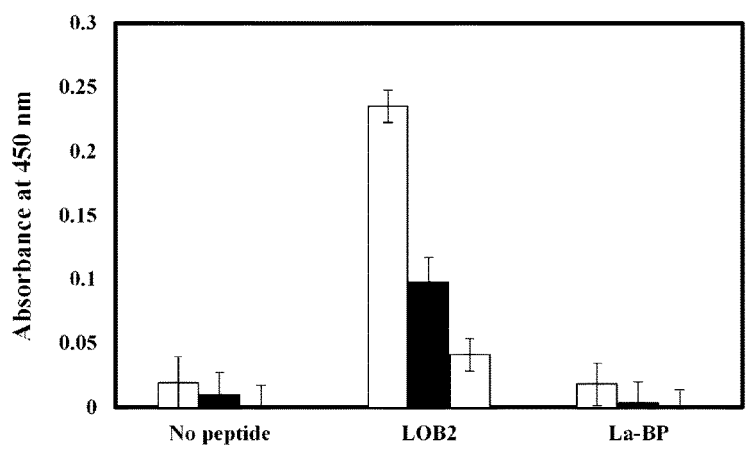
Evaluation of the ability of the LOB2 synthetic peptide binding to Dy$_2$O$_3$

[Fig. 5]
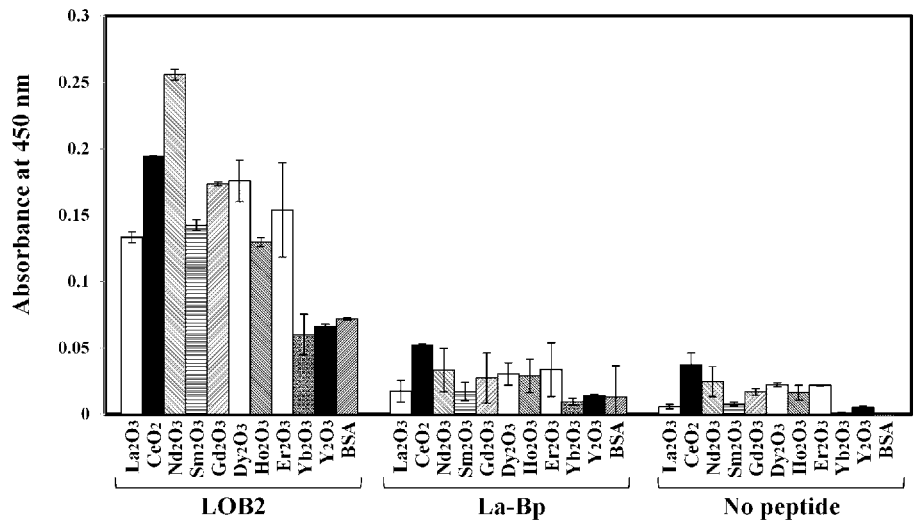
Evaluation of bindng specificity of the LOB2 synthetic peptide
[Fig. 6]
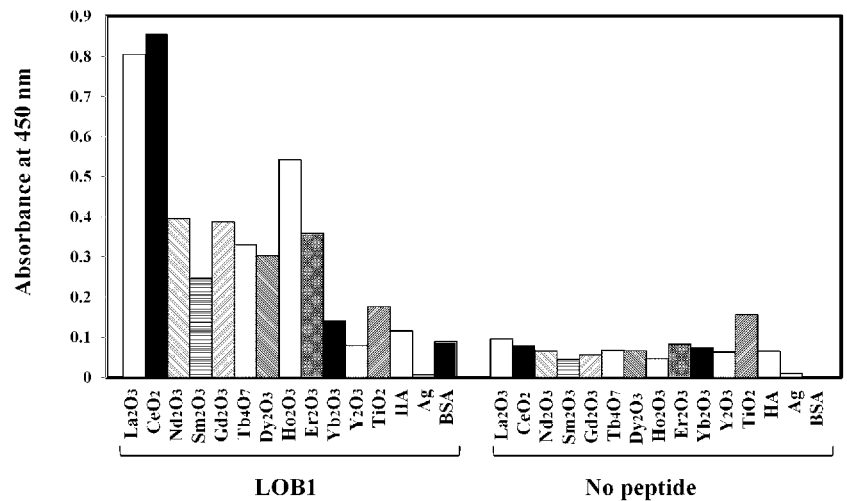
Evaluation of bindng specificity of the LOB1 synthetic peptide

[Fig. 7]

Alanine substitution test of the LOB2 peptide

| Phaeg Clone | Sequence |
|---|---|
| LOB2 | S C L W G D V S E L D F L C S |
| LOB2-1SA | A C L W G D V S E L D F L C S |
| LOB2-2CA | S A L W G D V S E L D F L C S |
| LOB2-3LA | S C A W G D V S E L D F L C S |
| LOB2-4WA | S C L A G D V S E L D F L C S |
| LOB2-5GA | S C L W A D V S E L D F L C S |
| LOB2-6DA | S C L W G A V S E L D F L C S |
| LOB2-7VA | S C L W G D A S E L D F L C S |
| LOB2-8SA | S C L W G D V A E L D F L C S |
| LOB2-9EA | S C L W G D V S A L D F L C S |
| LOB2-10LA | S C L W G D V S E A D F L C S |
| LOB2-11DA | S C L W G D V S E L A F L C S |
| LOB2-12FA | S C L W G D V S E L D A L C S |
| LOB2-13LA | S C L W G D V S E L D F A C S |
| LOB2-14CA | S C L W G D V S E L D F L A S |
| LOB2-15SA | S C L W G D V S E L D F L C A |

[Fig. 8]

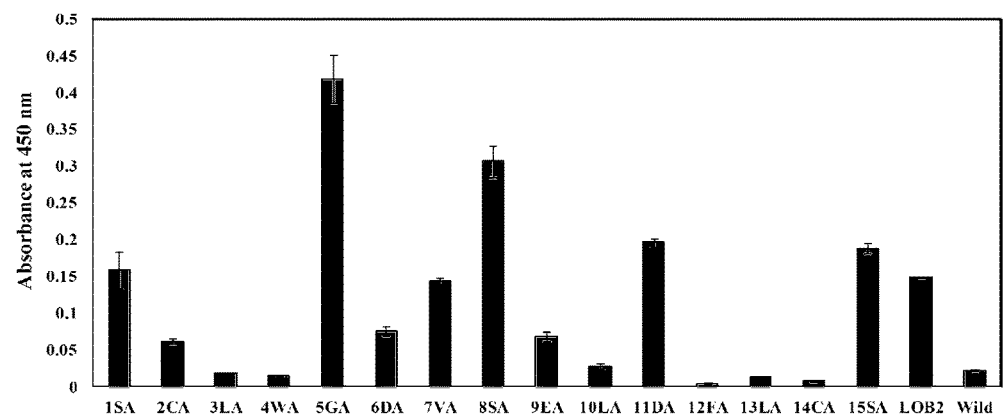

Alanine substitution test of the LOB2 peptide

[Fig. 9]

Amino acid sequences screened from a partial mutant library of the LOB2 peptide

| Phage Clone | Sequence | Frequency |
|---|---|---|
| LOB2 | S C L W G D V S E L D F L C S | 1/12 |
| 10 | S C L W I E S L D L D G L C S | 1/12 |
| 50 | S C L C C E V S D L G L V C S | 1/12 |
| 44 | S C V C I E R R E L D L L C S | 1/12 |
| 14 | S C I D S Y V G E L E T L G S | 1/12 |
| 19 | S C L W R A V C D L G I E C S | 1/12 |
| 41 | S C L G G D M S D K P V S C S | 1/12 |
| 12 | S C T C G M V N D V D L T C S | 1/12 |
| 2-30 | S C I V G E V R L S D L V C S | 1/12 |
| 12 | S C T C G M V N D V D L T C S | 1/12 |
| 9, 11 | S C V W R G F K D G Q W F C S | 2/12 |
| 42 | S C V C R G L R D L A H N C S | 1/12 |

[Fig. 10]

Amino acid sequences screened from a partial mutant library of the LOB1 peptide

| phage clone | Sequence | frequency |
|---|---|---|
| LOB1 | S C L Y P S W S D Y A F C S | 1/15 |
| 62 | S C T D P S W G E Y G F C S | 1/15 |
| 8 | S C E Y S S A S E Y A R C S | 1/15 |
| 1-26 | S C I Y G E W R D Y A F C S | 1/15 |
| 63 | S C V Y L S G S E C T F C S | 1/15 |
| 61 | S C L N A R W S D S P V C S | 1/15 |
| 1-34 | S C L N T I W A D Y G L G S | 1/15 |
| 77 | S C V D V S W G D I A C C S | 1/15 |
| 1-35 | S C F E F S W S E D C A C S | 1/15 |
| 1-27 | S W E R G S W C E D A C C S | 1/15 |
| 10 | S C V Y T G W R E D A S C S | 1/15 |
| 12 | S C C F A S C T D S A L C S | 1/15 |
| 13 | S C T R S R C G E G A F C S | 1/15 |
| 1-31 | S W Y V A I M S D K S F C S | 1/15 |
| 16 | S C I E A R Y T D H A L C S | 1/15 |

[Fig. 11]
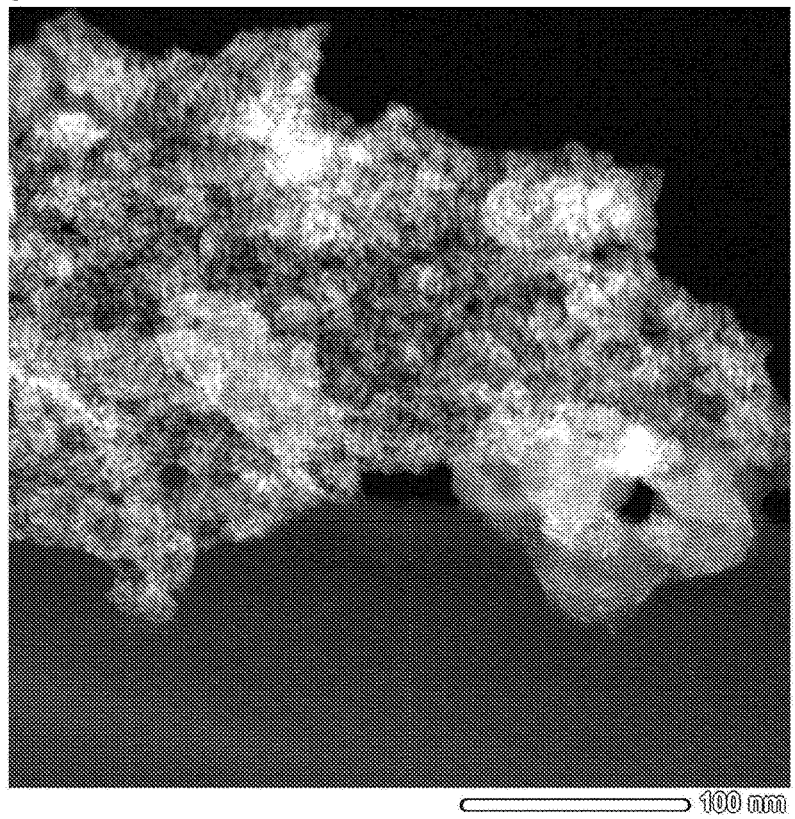
[Fig. 12]
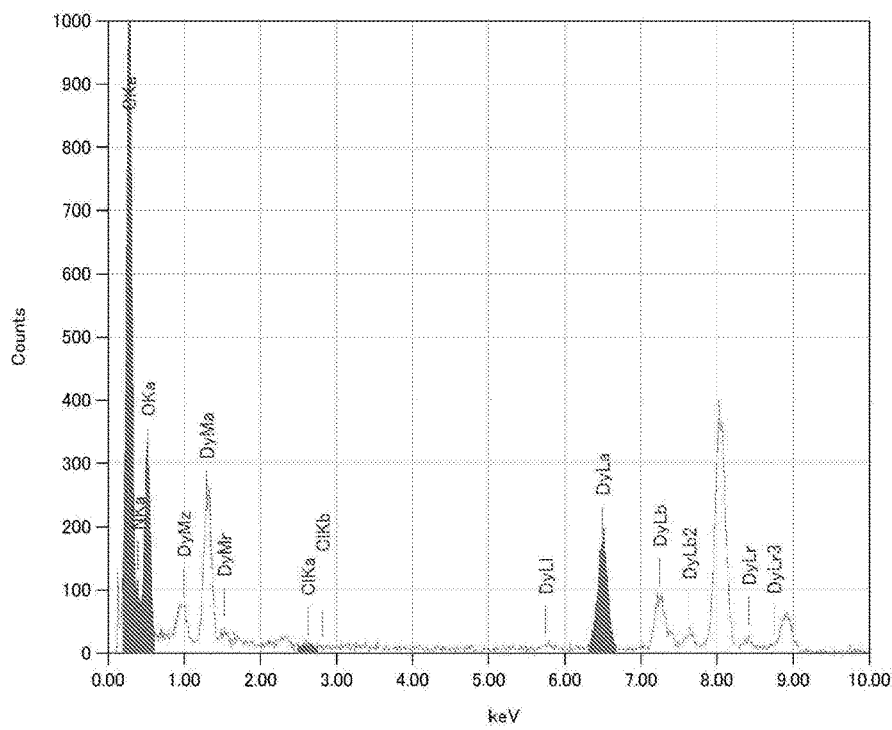
Elemental analysis of particles produced

[Fig.13A]
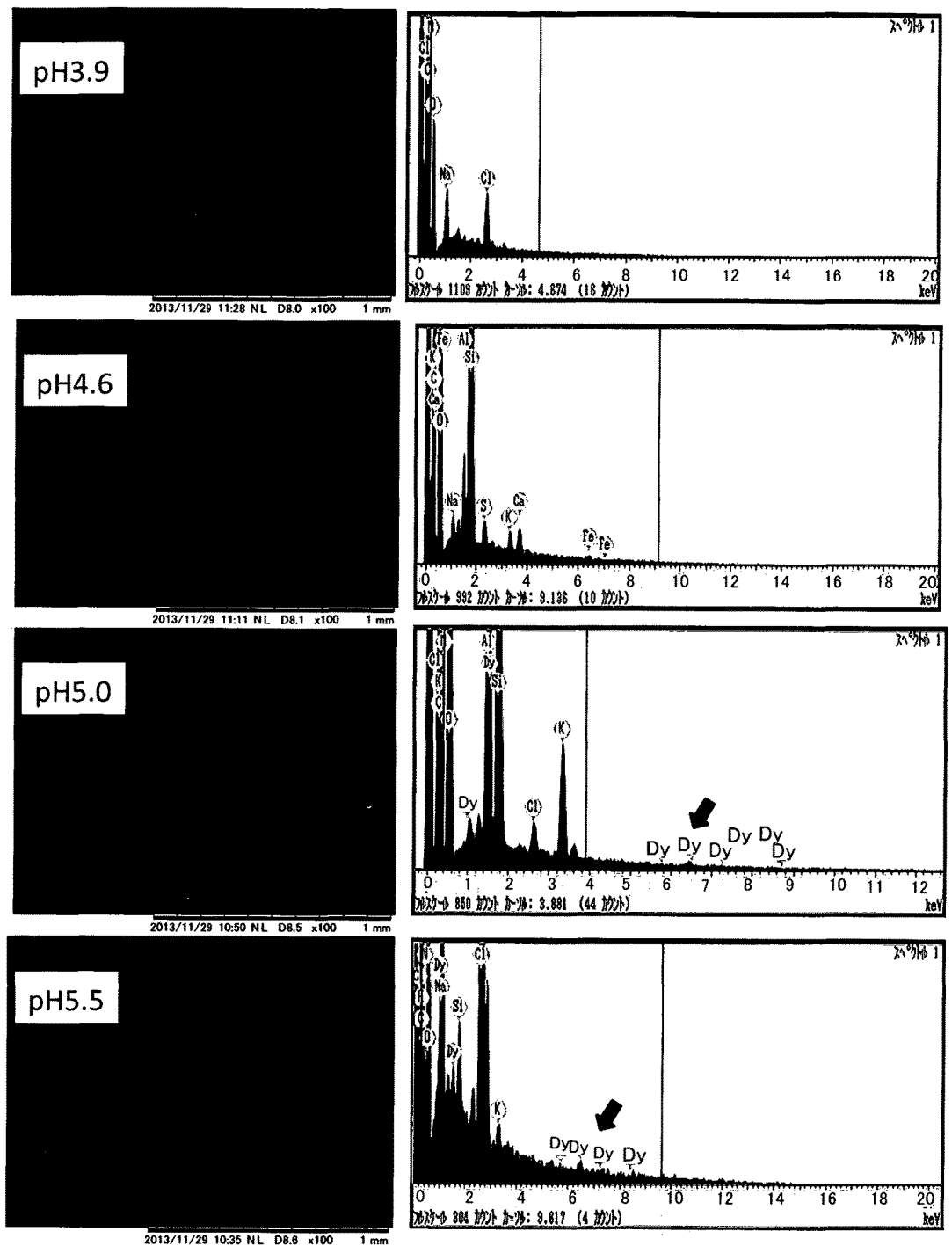
Effect of incubation pH on the mineralization activity

[Fig.13B]
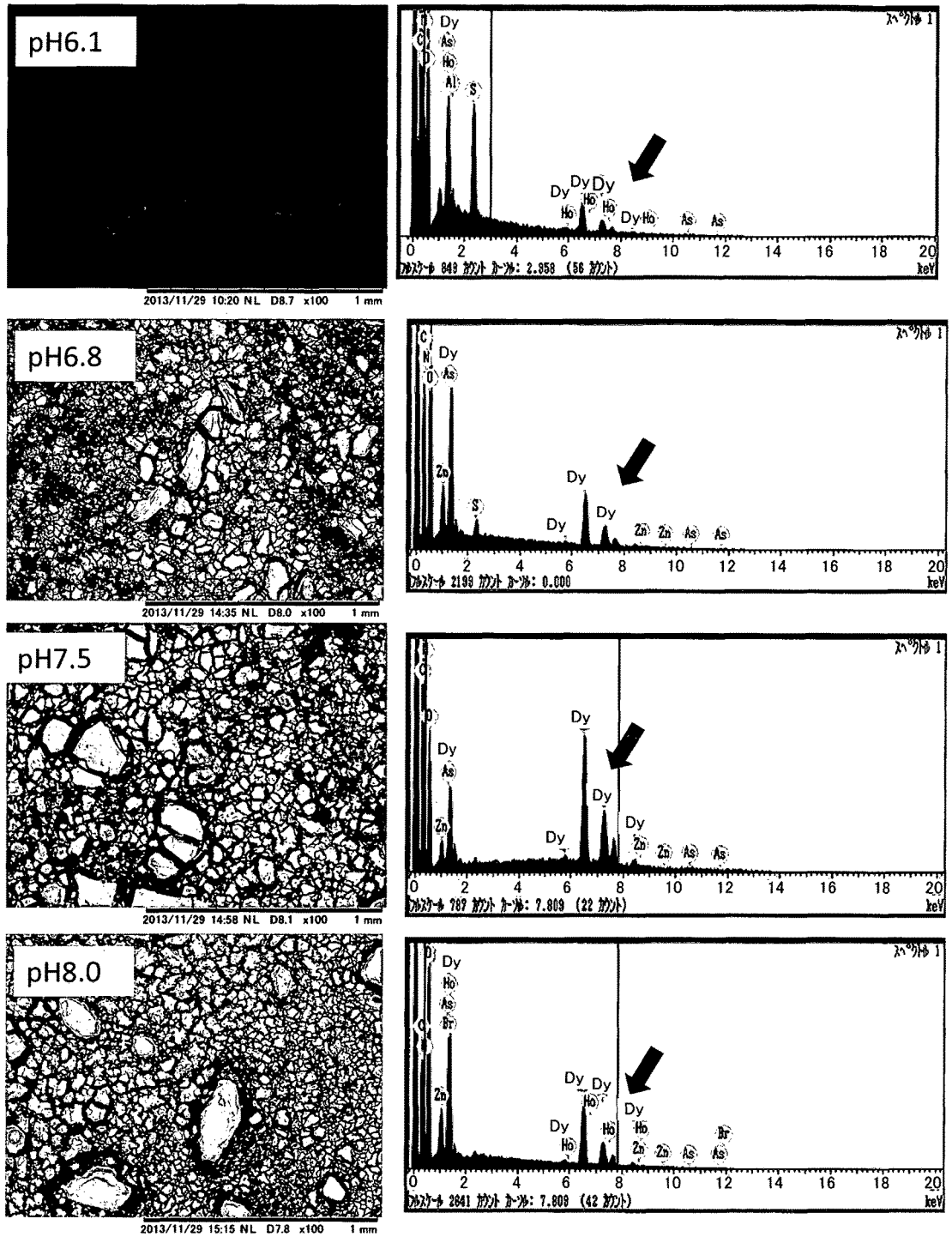
Effect of incubation pH on the mineralization activity

[Fig.14A]
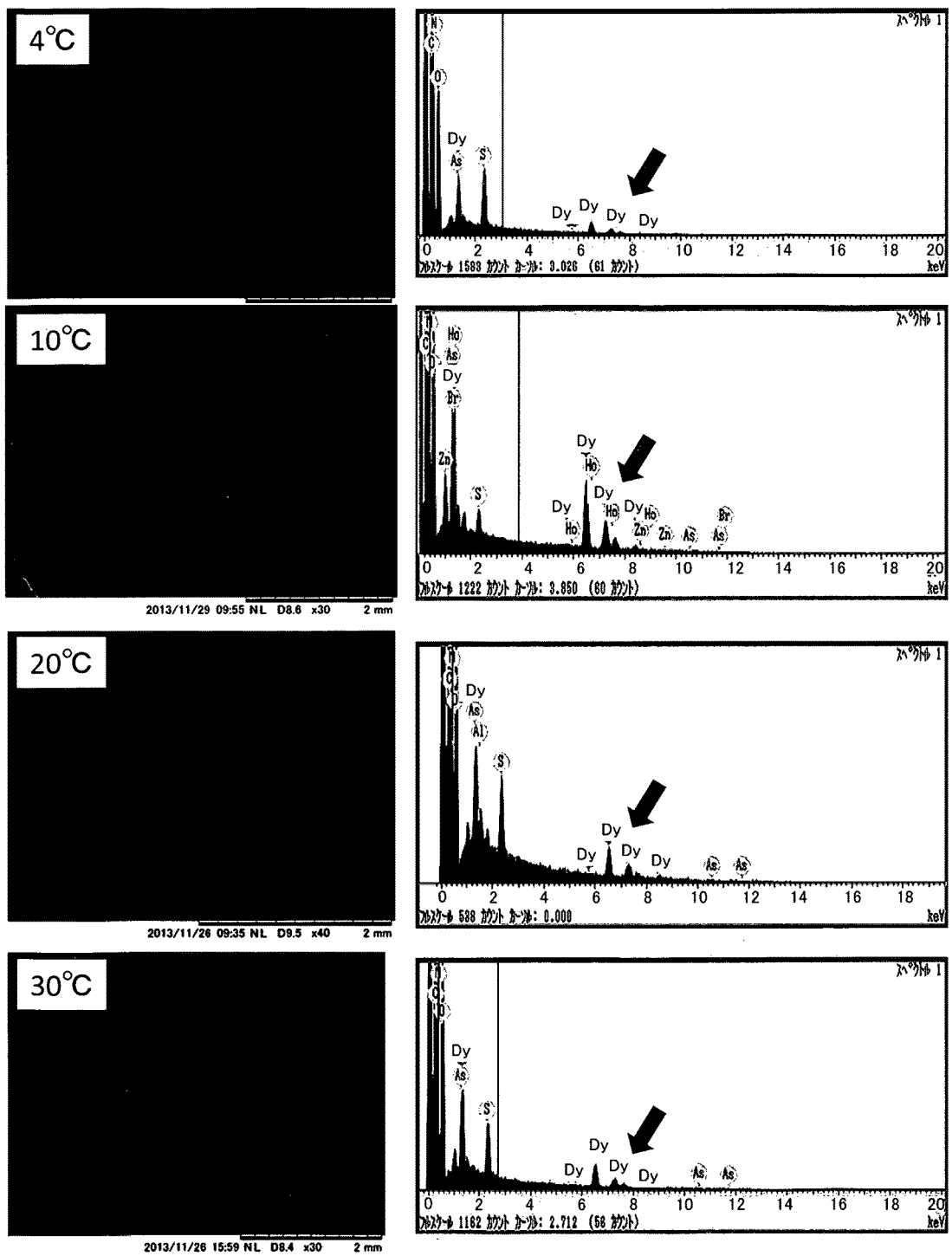
Effect of incubation temperature on the mineralization activity

[Fig.14B]
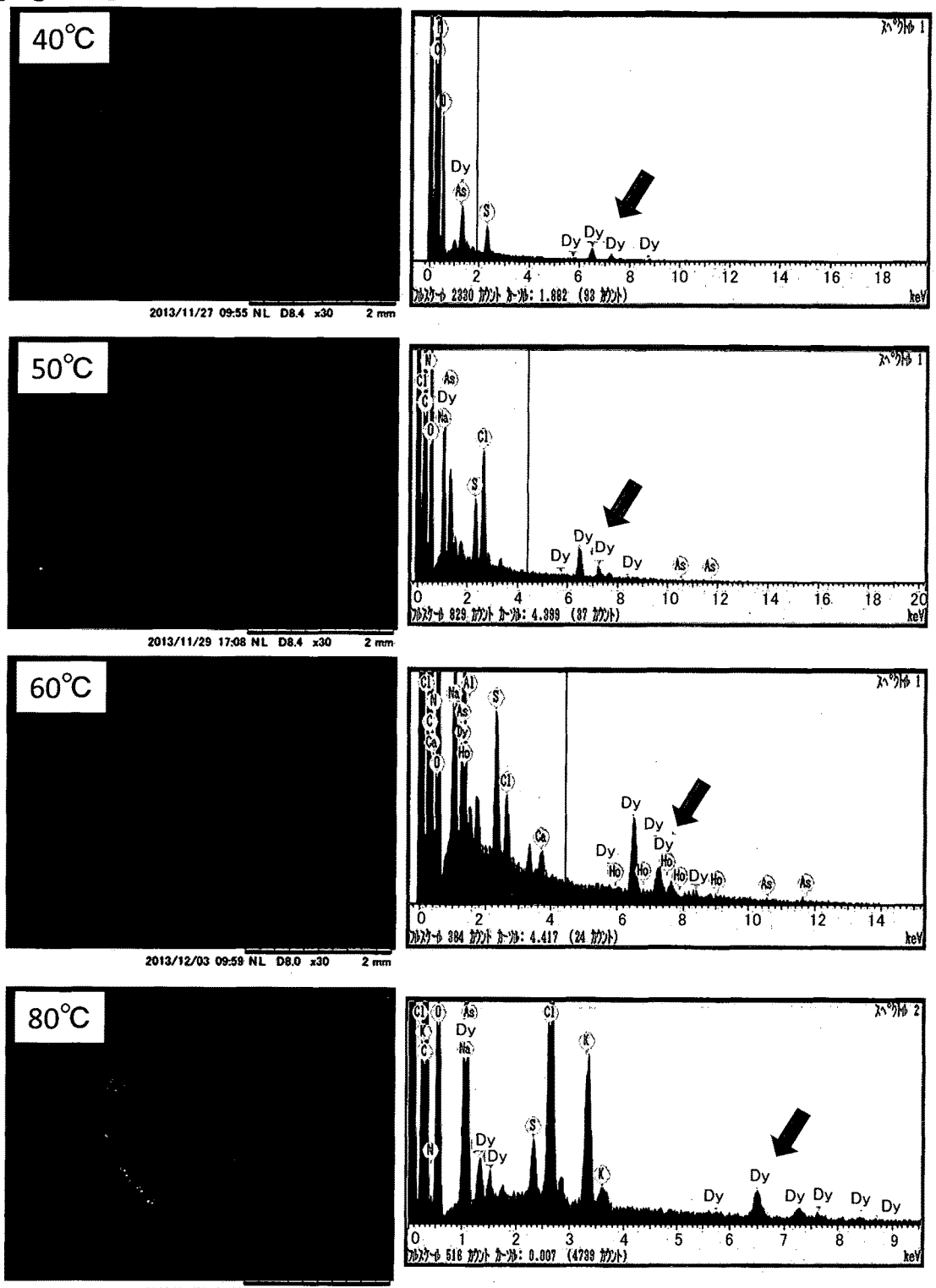
Effect of incubation temperature on the mineralization activity

[Fig. 15]
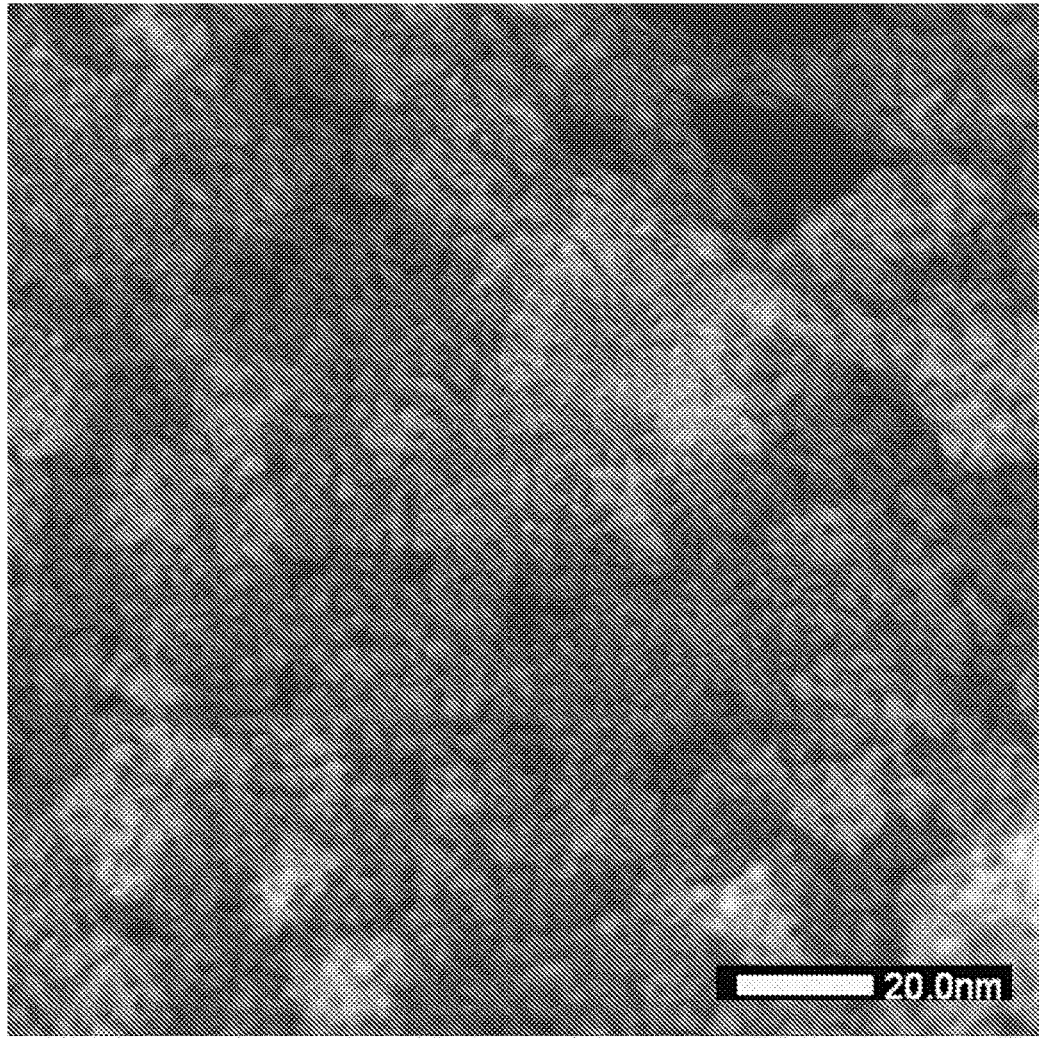
TEM image of particles produced

RARE EARTH MATERIAL-BINDING PEPTIDE AND USE THEREOF

TECHNICAL FIELD

The present specification relates to a rare earth material peptide and use thereof.

BACKGROUND ART

In recent years, exploitation of inorganic elements mainly including rare earths has been indispensable. Meanwhile stable supply of rare earths and the environmental impacts by rare earths also pose concerns. Therefore there is a need to develop techniques that allow effective collection of rare earths from nature and for establishment of techniques that allow low-energy, selective and effective recovery and recycling of rare earths contained in a subtle amount in discarded products and waste water.

Methods for recovering rare earths reported are methods in which rare earth elements are recovered by solvent extraction utilizing N,N-dioctyldiglycol amic acid (DOD-GAA) and the like or by utilizing reducing microorganisms. In addition, peptides that bind to cerium oxide have been described (Patent Literature 1). Peptides that bind to metal oxides such as zinc oxide have also been described (Patent Literature 2). Further, peptides that bind to gold, silver, platinum and the like have been described (Patent Literature 1 and Non Patent Literatures 1 and 2). It has been known that the metal-binding peptides have an ability to form metal nanoparticles under normal temperature by reduction (mineralization activity).

For example, dysprosium is a lanthanoid series rare earth and is a component metal of dysprosium oxide used for permanent magnets in hybrid vehicles and for magneto-optical disks.

CITATION LIST

Patent Literature

[Patent Literature 1] Japanese Patent Application Publication No. 2012-193155
[Patent Literature 2] Japanese Patent Application Publication No. 2013-509452

Non Patent Literature

[Non Patent Literature 1] Nature Chemistry, Vol. 29, p.393-399, 2011
[Non Patent Literature 2] Advanced Materials, Vol, 19, p.2492-2498, 2007

SUMMARY OF INVENTION

The methods utilizing solvent extraction and reducing microorganisms as described above are not always profitable in terms of the cost. In addition, no peptide has been described that recognizes rare earths or binds to oxides of rare earth metals such as dysprosium oxide.

The disclosure herein provides a peptide and use thereof that binds to a rare earth material such as rare earth metals and rare earth-containing inorganic compounds containing rare earth metals.

The inventors of the present invention used random peptide libraries by phage display to search peptides that bind to dysprosium oxide and obtained information on features of peptides that are useful for binding to dysprosium oxide. The present inventors also confirmed that the peptides bind to inorganic compounds of rare earths other than dysprosium oxide and to dysprosium ion. Based on such knowledge, the disclosure herein may provide the following.

(1) A rare earth material-binding agent including a peptide capable of binding to a rare earth material including a rare earth and a rare earth inorganic compound.

(2) The binding agent according to (1), wherein the peptide includes one or more acidic amino acid residues.

(3) The binding agent according to (2), wherein the peptide includes 2 or more acidic amino acid residues.

(4) The binding agent according to (2) or (3), wherein the amino acid residue is selected from glutamic acid and aspartic acid.

(5) The binding agent according to any of (1) to (4), wherein the peptide is a peptide with 10 or more to 20 or less amino acid residues.

(6) The binding agent according to any of (1) to (5), wherein the peptide is a cyclic peptide.

(7) The binding agent according to any of (1) to (6), wherein the peptide has an amino acid sequence of any of the following (1) and (2):

(1)
(SEQ ID NO: 1)
-X1-X2-X3-A1-X4-X5-A2-X6-A3-X7-X8- wherein A1 is an acidic amino acid, tyrosine, alanine, methionine or glycine; A2 is an acidic amino acid or leucine; A3 is an acidic amino acid, glycine, proline, glutamine or alanine; X1 is leucine, isoleucine, valine or threonine; X2 is tryptophan, cysteine, aspartic acid, glycine or valine; X3 is glycine, isoleucine, cysteine, serine or arginine; X4 is valine, serine, arginine, methionine, phenylalanine or leucine; X5 is serine, leucine, arginine, glycine, cysteine, asparagine or lysine; X6 is leucine, lysine, valine, serine or glycine; X7 is phenylalanine, glycine, leucine, threonine, isoleucine, valine, tryptophan or histidine; and X8 is leucine, valine, threonine, serine, asparagine, phenylalanine or glutamic acid, provided that at least one acidic amino acid is included;

(2)
(SEQ ID NO: 2)
-X11-X12-X13-X14-X15-X16-A4-X17-X18-X19- wherein A4 is an acidic amino acid; X11 is leucine, threonine, glutamic acid, isoleucine, valine, phenylalanine, cysteine or tyrosine; X12 is tyrosine, aspartic acid, asparagine, glutamic acid, arginine, phenylalanine or valine; X13 is proline, serine, glycine, leucine, alanine, threonine, valine or phenylalanine; X14 is serine, glutamic acid, arginine or isoleucine; X15 is tryptophan, alanine, glycine, cysteine, methionine or tyrosine; X16 is serine, glycine, threonine, alanine, arginine or cysteine; X17 is tyrosine, cysteine, serine, isoleucine, aspartic acid, serine, glycine, lysine or histidine; X18 is alanine, glycine, threonine, proline, cysteine or serine; and X19 is phenylalanine, arginine, valine, leucine, cysteine, alanine or serine.

(8) The binding agent according to (7), having an amino acid sequence represented by Leu-Trp-Gly-Asp/Glu-Val-Ser/Asn-Asp/Glu-Leu/Val-Asp/Glu-Phe/Leu-Leu.

(9) The binding agent according to (7), having an amino acid sequence represented by Leu-Tyr-Pro/Ala-Ser/Arg-Trp-Ser/Gly/Thr/Arg-Asp/Glu-Tyr/Asp-Ala/Gly-Phe/Leu.

(10) The binding agent according to any of (1) to (9), wherein the rare earth is one or more selected from the group consisting of lanthanum (La), cerium (Ce), neodymium (Nd), samarium (Sm), gadolinium (Gd), terbium (Tb), dysprosium (Dy), holmium (Ho) and erbium (Er).

(11) The binding agent according to any of (1) to (10), wherein the rare earth is dysprosium and the binding agent binds to a dysprosium ion and an oxide of dysprosium.

(12) The binding agent according to any of (1) to (11), wherein the peptide includes a label substance.

(13) A peptide having an amino acid sequence of the following (1) or (2):

(1)
(SEQ ID NO: 1)
-X1-X2-X3-A1-X4-X5-A2-X6-A3-X7-X8- wherein A1 is an acidic amino acid, tyrosine, alanine, methionine or glycine; A2 is an acidic amino acid or leucine; A3 is an acidic amino acid, glycine, proline, glutamine or alanine; X1 is leucine, isoleucine, valine or threonine; X2 is tryptophan, cysteine, aspartic acid, glycine or valine; X3 is glycine, isoleucine, cysteine, serine or arginine; X4 is valine, serine, arginine, methionine, phenylalanine or leucine; X5 is serine, leucine, arginine, glycine, cysteine, asparagine or lysine; X6 is leucine, lysine, valine, serine or glycine; X7 is phenylalanine, glycine, leucine, threonine, isoleucine, valine, tryptophan or histidine; and X8 is leucine, valine, threonine, serine, asparagine, phenylalanine or glutamic acid, provided that at least one acidic amino acid is included;

(2)
(SEQ ID NO: 2)
-X11-X12-X13-X14-X15-X16-A4-X17-X18-X19- wherein A4 is an acidic amino acid; X11 is leucine, threonine, glutamic acid, isoleucine, valine, phenylalanine, cysteine or tyrosine; X12 is tyrosine, aspartic acid, asparagine, glutamic acid, arginine, phenylalanine or valine; X13 is proline, serine, glycine, leucine, alanine, threonine, valine or phenylalanine; X14 is serine, glutamic acid, arginine or isoleucine; X15 is tryptophan, alanine, glycine, cysteine, methionine or tyrosine; X16 is serine, glycine, threonine, alanine, arginine or cysteine; X17 is tyrosine, cysteine, serine, isoleucine, aspartic acid, serine, glycine, lysine or histidine; X18 is alanine, glycine, threonine, proline, cysteine or serine; and X19 is phenylalanine, arginine, valine, leucine, cysteine, alanine or serine.

(14) The peptide according to (13), having an amino acid sequence represented by Leu-Trp-Gly-Asp/Glu-Val-Ser/Asn-Asp/Glu-Leu/Val-Asp/Glu-Phe/Leu-Leu.

(15) The peptide according to (13), having an amino acid sequence represented by Leu-Tyr-Pro/Ala-Ser/Arg-Trp-Ser/Gly/Thr/Arg-Asp/Glu-Tyr/Asp-Ala/Gly-Phe/Leu.

(16) A complex of a peptide capable of binding to a rare earth material including a rare earth and a rare earth inorganic compound, and the rare earth material.

(17) A method for producing a complex of a peptide capable of binding to a rare earth material including a rare earth and a rare earth inorganic compound, and the rare earth material, comprising the step of:
bringing the peptide into contact with the rare earth material to form the complex.

(18) A method for recovering a rare earth or an inorganic compound thereof, comprising the steps of:
bringing a peptide capable of binding to a rare earth material including a rare earth and a rare earth inorganic compound into contact with the rare earth material to form a complex of the peptide and the rare earth material; and
recovering the complex.

(19) A method for detecting a rare earth or an inorganic compound thereof, comprising the steps of:
bringing a peptide capable of binding to a rare earth material including a rare earth and a rare earth inorganic compound into contact with the rare earth material to form a complex of the peptide and the rare earth material; and
detecting the complex.

(20) A method for screening a peptide capable of binding to a rare earth material including a rare earth or a rare earth inorganic compound, comprising the step of: bringing one or more rare earth materials into contact with one or more test peptides to evaluate an ability of the one or more test peptides to bind to the one or more rare earth materials.

(21) A method for producing a rare earth-containing inorganic compound, comprising the step of:
bringing a rare earth ion serving as a starting material of the rare earth-containing inorganic compound into contact with another starting material of the rare earth-containing inorganic compound in a liquid medium and in the presence of a peptide capable of binding to a rare earth material including a rare earth and a rare earth inorganic compound to produce the rare earth-containing inorganic compound.

BRIEF DESCRIPTION OF DRAWINGS

FIG. 1 illustrates an overview of biopanning by phage display.

FIG. 2 illustrates the results of measurement of dysprosium oxide-binding phage titer in relation to the number of cycles of biopanning.

FIG. 3 illustrates the results of evaluation of the ability of monoclonal phages to bind to dysprosium oxide.

FIG. 4 illustrates the results of evaluation of the ability of the LOB2 peptide to bind to dysprosium oxide.

FIG. 5 illustrates the results of evaluation of binding specificity of the LOB2 peptide.

FIG. 6 illustrates the results of evaluation of binding specificity of the LOB1 peptide.

FIG. 7 illustrates amino acid sequences of alanine substituents of the LOB2 peptide.

FIG. 8 illustrates the results of evaluation of binding of alanine substituents of the LOB2 peptide to dysprosium oxide.

FIG. 9 illustrates the results of amino acid sequence analysis of peptides screened from a partial mutant library of the LOB2 peptide using the binding ability to dysprosium oxide as an index.

FIG. 10 illustrates the results of amino acid sequence analysis of peptides screened from a partial mutant library of the LOB 1 peptide using the binding ability to dysprosium oxide as an index.

FIG. 11 illustrates the result of TEM observation of particles produced after the LOB2 peptide was brought into contact with dysprosium ion.

FIG. 12 illustrates the result of EDX analysis of particles produced after the LOB2 peptide was brought into contact with dysprosium ion.

FIG. 13A illustrates an effect of incubation pH on the mineralization activity of the LOB2 peptide.

FIG. 13B illustrates an effect of incubation pH on the mineralization activity of the LOB2 peptide.

FIG. 14A illustrates an effect of incubation temperature on the mineralization activity of the LOB2 peptide.

FIG. 14B illustrates an effect of incubation temperature on the mineralization activity of the LOB2 peptide.

FIG. 15 illustrates the result of TEM observation of dysprosium oxide obtained by mineralization using the LOB2 peptide.

DESCRIPTION OF EMBODIMENTS

The disclosure herein relates to a peptide capable of binding to a rare earth or an inorganic compound thereof and to use thereof.

A peptide of the disclosure herein can bind to a rare earth material which is a rare earth or a metal oxide thereof to form a complex. Therefore according to the present binding agent, a rare earth material can be retained, detected and recovered with the peptide.

As used herein, "rare earth material" includes a rare earth and an inorganic compound thereof.

As used herein, "rare earth" includes both scandium (Sc) and yttrium (Y) as well as lanthanoid elements, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu).

As used herein, a rare earth includes metal single substances as well as ions having valences equal to possible oxidation numbers of respective rare earths.

As used herein, an inorganic compound of a rare earth includes oxides, hydroxides, inorganic acid salts and organic acid salts of respective rare earths having possible oxidation numbers thereof.

(Rare Earth Material-binding Peptide)

Binding between a rare earth material-binding peptide (hereinafter merely referred to as "the present peptide") as disclosed herein and a rare earth material means the status where the peptide and the rare earth material are bound by means of an interaction other than covalent bonding, so that they are obtained as a complex. Typically, the binding includes the status where the present peptide is bound to a rare earth ion or a rare earth inorganic compound in a liquid medium. The interaction generally includes electrostatic binding, ion binding, hydrogen binding and the like; however the "binding" as used herein is not limited thereto.

The present peptide may bind to a rare earth or a cation thereof or to an inorganic compound of a rare earth. The present peptide may bind to one rare earth or a cation thereof and/or an inorganic compound such as an oxide of the rare earth. The present peptide may bind to two or more rare earths or cations thereof and/or inorganic compounds of the two or more rare earths. The present peptide may bind to 3 or more, preferably 4 or more and more preferably 5 or more rare earths or cations thereof and/or inorganic compounds of the rare earths.

The present peptide is capable of binding to a rare earth material. The present inventors believe that a carboxy group of an acidic amino acid residue in the peptide contributes to binding thereof to a rare earth material.

As used herein, the term "peptide" is a polymer of generally a few or more natural amino acids and/or non-natural amino acids linked via acid amide bonds. A peptide generally has 100 or less amino acid residues. Preferably, a rare earth-binding sequence of the present peptide has 5 or more amino acid residues, for example, more preferably 7 or more and still more preferably 8 or more. The upper limit of the amino acid residues is not particularly limited and, in consideration of the binding ability to a rare earth material, may be 25 or less, 20 or less or 15 or less.

The present peptide is preferably a polymer of L-amino acid residues. However, a polymer of D-amino acids is not excluded.

A peptide is generally linear. The present peptide may be linear or may be cyclic by means of an intramolecular disulfide bond or the like. In this case, it is preferable that the peptide is cyclized at a position that is outside of an amino acid sequence (hereinafter merely referred to as "rare earth-binding sequence"; for example, an amino acid sequence including an acidic amino acid residue and appropriate number of amino acid residues upstream and downstream thereof) which may contribute to the binding to a rare earth material. Typically a peptide including a rare earth-binding sequence flanked by cysteine residues can be cyclized in the presence of an oxidizing agent such as iodine or hydrogen peroxide.

A rare earth or a rare earth in an inorganic compound thereof to which the present peptide binds is preferably one or more selected from the group consisting of lanthanum (La), cerium (Ce), neodymium (Nd), samarium (Sm), gadolinium (Gd), terbium (Tb), dysprosium (Dy), holmium (Ho) and erbium (Er). More preferably the rare earth is lanthanum, cerium, neodymium, samarium, gadolinium, terbium, dysprosium, holmium or erbium and more preferably lanthanum, cerium, neodymium, samarium, gadolinium, terbium or dysprosium.

The present peptide can bind to one or more rare earths and/or inorganic compounds thereof. A binding ability of the present peptide to a rare earth and an inorganic compound thereof varies depending on the amino acid sequence. Thus one rare earth-binding sequence may bind to cerium with high selectivity while the other rare earth-binding sequence may bind to lanthanum with high selectivity. There may be a rare earth-binding sequence specifically binding to an inorganic compound. Therefore a rare earth to which the present peptide is applied may be selected depending on the binding ability of the rare earth-binding sequence used. It is inferred that the binding ability of a rare earth-binding sequence to a rare earth is ensured by inclusion of an acidic amino acid residue and it is believed that the binding strength, the type of the rare earth or inorganic compound thereof to which the sequence binds may vary in some extent depending on the amino acid sequence including the acidic amino acid residue.

A rare earth-binding sequence in the present peptide preferably includes one or more acidic amino acid residues and more preferably two or three or more acidic amino acid residues. Examples of an acidic amino acid residue include glutamic acid, aspartic acid, isoaspartic acid, isoglutamic acid, 2-aminoadipic acid, 2-aminosuberic acid and the like. Aspartic acid or glutamic acid is preferred. Two or more acidic amino acid residues may be the same or different.

When the present peptide includes two or more acidic amino acid residues, the acidic amino acid residues in the closest vicinity may be directly adjacent to each other or may be intervened by one or more amino acid residues. The intervening amino acid residue is not particularly limited and is preferably a neutral amino acid residue, an aromatic amino acid residue and the like. The intervening amino acid residue more preferably includes a neutral amino acid residue.

The neutral amino acid residue as used herein includes glycine, alanine, valine, leucine, isoleucine, serine, threonine and norvaline. The basic amino acid residue includes lysine, norleucine, 2-aminobutanoic acid, methionine, o-methylserine, t-butylglycine, t-butylalanine and cyclohexylalanine. The acid amide amino acid residue includes asparagine and glutamine. The basic amino acid residue includes lysine, arginine, ornithine, 2,4-diaminobutanoic acid and 2,3-diaminopropionic acid. The cyclic amino acid residue includes proline, 3-hydroxyproline and 4-hydroxyproline. The OH-containing amino acid residue includes serine, threonine and homoserine. The aromatic amino acid residue includes phenylalanine, tyrosine and tryptophan.

The present peptide may have a rare earth-binding sequence for example including the following (1) or (2):

(1)
(SEQ ID NO: 1)
-X1-X2-X3-A1-X4-X5-A2-X6-A3-X7-X8- wherein A1 is an acidic amino acid, tyrosine, alanine, methionine or glycine; A2 is an acidic amino acid or leucine; A3 is an acidic amino acid, glycine, proline, glutamine or alanine; X1 is leucine, isoleucine, valine or threonine; X2 is tryptophan, cysteine, aspartic acid, glycine or valine; X3 is glycine, isoleucine, cysteine, serine or arginine; X4 is valine, serine, arginine, methionine, phenylalanine or leucine; X5 is serine, leucine, arginine, glycine, cysteine, asparagine or lysine; X6 is leucine, lysine, valine, serine or glycine; X7 is phenylalanine, glycine, leucine, threonine, isoleucine, valine, tryptophan or histidine; and X8 is leucine, valine, threonine, serine, asparagine, phenylalanine or glutamic acid, provided that at least one acidic amino acid is included;

(2)
(SEQ ID NO: 2)
-X11-X12-X13-X14-X15-X16-A4-X17-X18-X19- wherein A4 is an acidic amino acid; X11 is leucine, threonine, glutamic acid, isoleucine, valine, phenylalanine, cysteine or tyrosine; X12 is tyrosine, aspartic acid, asparagine, glutamic acid, arginine, phenylalanine or valine; X13 is proline, serine, glycine, leucine, alanine, threonine, valine or phenylalanine; X14 is serine, glutamic acid, arginine or isoleucine; X15 is tryptophan, alanine, glycine, cysteine, methionine or tyrosine; X16 is serine, glycine, threonine, alanine, arginine or cysteine; X17 is tyrosine, cysteine, serine, isoleucine, aspartic acid, serine, glycine, lysine or histidine; X18 is alanine, glycine, threonine, proline, cysteine or serine; and X19 is phenylalanine, arginine, valine, leucine, cysteine, alanine or serine.

The rare earth-binding sequence (1) has high binding ability to lanthanum, cerium, neodymium, samarium, gadolinium, dysprosium, holmium, erbium or an oxide of any of the foregoing, has high binding ability to, inter alia, cerium, neodymium, gadolinium, dysprosium and erbium or an oxide of any of the foregoing and has further high binding ability to cerium and neodymium or an oxide of any of the foregoing.

The rare earth-binding sequence (2) has high binding ability to lanthanum, cerium, neodymium, samarium, gadolinium, terbium, dysprosium, holmium, erbium or an oxide of any of the foregoing, has high binding ability to, inter alia, lanthanum, cerium, holmium or an oxide of any of the foregoing and has further high binding ability to lanthanum and cerium or an oxide of any of the foregoing.

The rare earth-binding sequences preferably have aspartic acid or glutamic acid as an acidic amino acid.

In the rare earth-binding sequence (1), X1 is preferably leucine, isoleucine or valine; X2 is preferably tryptophan or cysteine; X3 is preferably glycine; A1 is preferably aspartic acid or glutamic acid; X4 is preferably valine; A2 is preferably glutamic acid or aspartic acid; X5 is preferably serine, arginine, asparagine or lysine; X6 is preferably leucine or valine; X7 is preferably phenylalanine or leucine; and X8 is preferably leucine, valine or threonine.

In the rare earth-binding sequence (2), X11 is preferably leucine, isoleucine, valine or threonine; X12 is preferably tyrosine, asparagine, aspartic acid, arginine or glutamic acid; X13 is preferably proline, alanine, serine or glycine; X14 is preferably serine, arginine or isoleucine; X15 is preferably tryptophan; X16 is preferably serine, glycine or threonine; X17 is preferably tyrosine, aspartic acid or serine; X18 is alanine, threonine or glycine; and X19 is preferably phenylalanine or leucine.

The rare earth-binding sequence (1) is preferably represented by
Leu/Val-Trp/Cys-Gly/Arg-Asp/Glu-Val-Ser/Asn/Lys/Arg-Asp/Glu-Leu/Val-Asp/Glu-Phe/Leu/Val-Leu/Val/Thr, more preferably by
Cys-Leu/Val-Trp/Cys-Gly/Arg-Asp/Glu-Val-Ser/Asn/Lys/Arg-Asp/Glu-Leu/Val-Asp/Glu-Phe/Leu/Val-Leu/Val/Thr-Cys and still more preferably by
Ser-Cys-Leu/Val-Trp/Cys-Gly/Arg-Asp/Glu-Val-Ser/Asn/Lys/Arg-Asp/Glu-Leu/Val-Asp/Glu-Phe/Leu/Val-Leu/Val/Thr-Cys-Ser.

The rare earth-binding sequence has high binding ability to cerium, neodymium, gadolinium, dysprosium and an oxide of any of the foregoing and further has high binding ability to cerium, neodymium and an oxide of any of the foregoing. The rare earth-binding sequence also has binding ability to dysprosium (ion).

The rare earth-binding sequence (2) is preferably represented by
Leu-Tyr-Pro/Ala-Ser/Arg-Trp-Ser/Gly/Thr/Arg-Asp/Glu-Tyr/Asp-Ala/Gly/Ser/Thr-Phe/Leu, more preferably by
Cys-Leu-Tyr-Pro/Ala-Ser/Arg-Trp-Ser/Gly/Thr/Arg-Asp/Glu-Tyr/Asp-Ala/Gly/Ser/Thr-Phe/Leu-Cys, and still more preferably by
Ser-Cys-Leu-Tyr-Pro/Ala-Ser/Arg-Trp-Ser/Gly/Thr/Arg-Asp/Glu-Tyr/Asp-Ala/Gly/Ser/Thr-Phe/Leu-Cys-Ser. The rare earth-binding sequence has high binding ability to lanthanum, cerium, holmium and an oxide of any of the foregoing and further has high binding ability to lanthanum, cerium and an oxide of any of the foregoing.

The rare earth-binding sequence may further include one or more additional amino acids at the N-terminal or C-terminal of the sequence. For example, 1 or 2 amino acids may be added, 1 or more and 3 or less amino acids may be added, 1 or more and 5 or less amino acids may be added, 1 or more and 7 or less amino acids may be added, 1 or more and 9 or less amino acids may be added and 1 or more and 10 or less amino acids may be added.

Examples of an amino acid which may be added to a terminal of the rare earth-binding sequence include serine, cysteine, asparagine and the like. By introducing cysteine at both terminals, the present peptide may be cyclized.

Examples of a peptide containing the rare earth-binding sequence (1) include peptides containing the following rare earth-binding sequences. In each of the peptides described below, the rare earth-binding sequence is preferably the one from which one amino acid residue at both N-terminal and C-terminal is removed and more preferably the one from which two amino acid residues, i.e. SC— and —CS, at both terminals are removed.

(SEQ ID NO: 3)
SerCys-LeuTrpGlyAspValSerGluLeuAspPheLeu-CysSer (SEQ ID NO: 4)
SerCys-LeuTrpIleGluSerLeuAspLeuAspGlyLeu-CysSer

```
                                          (SEQ ID NO: 5)
SerCys-LeuCysCysGluValSerAspLeuGlyLeuVal-CysSer (SEQ ID NO: 6)
SerCys-ValCysIleGluArgArgGluLeuAspLeuLeu-CysSer (SEQ ID NO: 7)
SerCys-IleAspSerTyrValGlyGluLeuGluThrLeu-CysSer (SEQ ID NO: 8)
SerCys-LeuTrpArgAlaValCysAspLeuGlyIleGlu-CysSer (SEQ ID NO: 9)
SerCys-LeuGlyGlyAspMetSerAspLysProValSer-CysSer (SEQ ID NO: 10)
SerCys-ThrCysGlyMetValAsnAspValAspLeuThr-CysSer (SEQ ID NO: 11)
SerCys-IleValGlyGluValArgLeuSerAspLeuVal-CysSer (SEQ ID NO: 12)
SerCys-ThrCysGlyMetValAsnAspValAspLeuThr-CysSer (SEQ ID NO: 13)
SerCys-ValTrpArgGlyPheLysAspGlyGlnTrpPhe-CysSer (SEQ ID NO: 14)
SerCys-ValCysArgGlyLeuArgAspLeuAlaHisAsn-CysSer
```

Examples of a peptide containing the rare earth-binding sequence (2) include peptides containing the following rare earth-binding sequences. In each of the peptides described below, the rare earth-binding sequence is preferably the one from which 3 amino acid residues at the N-terminal and 2 amino acid residues at the C-terminal are removed and more preferably the one from which SC— and —CS at both terminals are removed.

```
                                          (SEQ ID NO: 15)
SerCys-LeuTyrProSerTrpSerAspTyrAlaPhe-CysSer (SEQ ID NO: 16)
SerCys-ThrAspProSerTrpGlyGluTyrGlyPhe-CysSer (SEQ ID NO: 17)
SerCys-GluTyrSerSerAlaSerGluTyrAlaArg-CysSer (SEQ ID NO: 18)
SerCys-IleTyrGlyGluTrpArgAspTyrAlaPhe-CysSer (SEQ ID NO: 19)
SerCys-ValTyrLeuSerGlySerGluCysThrPhe-CysSer (SEQ ID NO: 20)
SerCys-LeuAsnAlaArgTrpSerAspSerProVal-CysSer (SEQ ID NO: 21)
SerCys-LeuAsnThrIleTrpAlaAspTyrGlyLeu-CysSer (SEQ ID NO: 22)
SerCys-LysAspValSerTrpGlyAspIleAlaCys-CysSer (SEQ ID NO: 23)
SerCys-PheGluPheSerTrpSerGluAspCysAla-CysSer (SEQ ID NO: 24)
SerCys-GluArgGlySerTrpCysGluAspAlaCys-CysSer (SEQ ID NO: 25)
SerCys-ValTyrThrGlyTrpArgGluAspAlaSer-CysSer (SEQ ID NO: 26)
SerCys-CysPheAlaSerCysThrAspSerAlaLeu-CysSer (SEQ ID NO: 27)
SerCys-ThrArgSerArgCysGlyAspGlyAlaPhe-CysSer (SEQ ID NO: 28)
SerCys-TyrValAlaIleMetSerGluLysSerPhe-CysSer (SEQ ID NO: 29)
SerCys-IleGluAlaArgTyrThrAspHisAlaLeu-CysSer
```

The present peptide can be obtained by any methods well known to a person skilled in the art including well known chemical synthesis methods as well as genetic engineering methods.

The present peptide may include a label substance. Inclusion of a label substance is convenient for recovery and the like because the present peptide bound to a rare earth can be identified. A label is not particularly limited and may be any well-known label substance. A label substance may be visibly distinguishable or may emit light by irradiation of light having certain wavelength. A label substance may be colored per se or may generate color by reaction with another compound. A label substance may be supported on a support such as a bead. Examples of such a label substance include a colored bead, gold colloid, a fluorescence compound, an enzyme protein and the like. A label substance encompasses a label-binding substance such as those utilizing antibody-antibody reaction and those utilizing biotin-avidin interaction. A label-binding substance is a substance binding to a label substance and can also serve as a label substance.

A label substance is attached according to any well-known methods. Typically a label substance is attached at the N-terminal and/or C-terminal of the present peptide via an appropriate number of linker peptides.

When two or more present peptides having different binding properties (binding selectivity and the like) towards a rare earth material are used, each peptide may include a distinct label substance.

The present peptide may include a tag so that the present peptide can be recovered by affinity chromatography and the like. A tag may be an antigen (epitope) and the like or may be a well-known His-tag, biotin or the like. A tag may be attached to the peptide via an appropriate linker By using an antibody directed against the present peptide, the present peptide can be identified without labeling.

As described above, the present peptide can be also used as a rare earth-binding agent capable of binding to a rare earth material.

(Mineralization Activity)

The present peptide has, in addition to the binding ability to a rare earth material, mineralization activity for producing a rare earth-containing inorganic compound from a rare earth ion. The mineralization activity is specifically described in the paragraphs hereinbelow.

According to the present specification, also provided is a fusion peptide or a fusion protein (hereinafter merely referred to as "fusion protein") including the present peptide or the rare earth-binding sequence and another peptide. In the fusion protein, the present peptide or the rare earth-binding sequence is fused so that the binding ability to a rare earth is at least substantially retained. Substantial retention of the binding ability to a rare earth refers to retention of the specificity of the original binding ability to a rare earth while retaining preferably 50% or more, more preferably 60% or more, still more preferably 70% or more, yet more preferably 80% or more and further more preferably 90% or more of the original binding strength. Whether or not a fusion protein retains the original binding ability to a rare earth can be confirmed by the manner described in Examples hereinbelow and the like.

Another peptide in the fusion protein may have a desired property or function. Any of various well known proteins such as antibodies, enzymes and membrane proteins may be selected as required. A person skilled in the art can obtain such a fusion protein by any well-known genetic engineering methods or chemical methods.

The fusion protein herein can have a comparable property or function as the present peptide and can be applied to similar applications.

According to the present specification, also provided is DNA such as nucleotides encoding the present peptide or the present fusion protein or a vector including the DNA for expressing the present peptide or the fusion protein. A person skilled in the art can easily obtain DNA based on the rare earth-binding sequence and the like described above and construct the expression vector according to any well-known methods. The expression vector contains elements selected according to the host cell used for expression of the present peptide or the fusion protein.

(Peptide-immobilized Solid Phase Support)

The present peptide may be supported on a solid phase support. The present peptide may be supported on, for example, granules such as a variety of beads or sheets made of various materials. Such a solid phase support is well known and a person skilled in the art can select and use an appropriate solid phase support. The mode and method of immobilization of the peptide on a solid phase support is well known. A person skilled in the art can select an appropriate immobilization method, select a desired mode (a pattern of immobilization onto a solid phase support in the form of sheet) and obtain a peptide-immobilized solid phase support. A solid phase support in the form of granules may carry the present peptide throughout the surface of the solid phase support typically by dipping and the like. A solid phase support in the form of a sheet may carry the present peptide so as to form a film or in any other arbitrary pattern by dipping, coating, spotting and the like.

When two or more present peptides having different binding properties (binding selectivity and the like) towards a rare earth material are immobilized on a solid phase support, the peptides may be respectively immobilized on granular solid phase supports which are distinctively identified, or the peptides may be respectively immobilized as spots at distinct positions on a solid phase support in the form of a sheet.

In addition, the present peptide may be accompanied by a biological support. Specifically, the present peptide may be presented on a surface layer of a biological support such as a cell or may form the surface layer. Examples of the biological support include various microorganisms, plant cells, animal cells, viruses, phages and the like. The present peptide may be presented on, for example, a surface layer of a microorganism such as yeast and Escherichia coli, or may form a coat protein of a phage or virus.

As described above, the present peptide can be used as, on the basis of the binding ability to a rare earth material, a binding agent of a rare earth material, a detecting agent (probe) of a rare earth material and a recovery agent (separating agent) of a rare earth material. For example, the peptide-immobilized solid phase support is useful for any of the applications. The present peptide-immobilized solid phase support is also useful as a device (array) for recovery or detection of a rare earth material.

The present peptide can be utilized as, on the basis of the mineralization activity, an agent for producing an inorganic compound of a rare earth from a rare earth ion. The peptide-immobilized solid phase support can also be utilized as the agent.

Based on the above, the present peptide, the present peptide containing a label substance and the like and the peptide-immobilized solid phase support (including a biological support) carrying the present peptide are useful per se.

(Binding between the Present Peptide and a Rare Earth Material)

In order to allow binding of the present peptide to a rare earth material, the present peptide may be brought into contact with the rare earth material. The condition for binding of the present peptide and a rare earth material is not particularly limited as far as the present peptide can exhibit the binding ability to the rare earth material. The binding status between the rare earth material and the present peptide is observed under various conditions in terms of pH, temperature and salt concentration and thus the binding condition can be established. For example, the present inventors have confirmed that the present peptide binds to a rare earth material at pH of 5 or higher and 8 or lower and a temperature in the range of 4 deg C. or higher and 80 deg C. or lower.

In order to allow binding of the present peptide to a rare earth material, the present peptide may be brought into contact with a rare earth-containing material in a liquid medium by mixing and the like. The liquid medium may be any liquid medium as far as it allows the present peptide to exhibit the binding ability to the rare earth material. The liquid medium may be an aqueous medium or an organic medium or a mixed medium of the foregoing. Typically, a buffer having around neutral pH or a mixed solution containing the buffer may be used. For example, pH may be, but not is particularly limited to, 5 or higher and 8 or lower. The salt concentration may be, but again not is particularly limited to, 10 mM or more and 1 M or less. The temperature is again not particularly limited and the binding can be easily obtained without temperature control. Typically, the temperature may be 4 deg C. or higher and 80 deg C. or lower, more preferably 10 deg C. or higher and 40 deg C. or lower and still more preferably 15 deg. C. or higher and 30 deg. C. or lower. The efficiency of contact between the present peptide and a rare earth material can be improved by appropriately stiffing. The period for bringing the present peptide and a rare earth material into contact may be, but is not particularly limited to, from around 10 minutes to a few hours and preferably 30 minutes or more and 8 hours or less. The upper limit for the period may be more preferably 6 hours or less and still more preferably around 4 hours or less. The period may be more preferably around 1 hour or more and 3 hours or less.

The concentration of the present peptide and the concentration of the rare earth material in the liquid medium in order to allow the present peptide to exhibit the binding ability to the rare earth material are not particularly limited. For example, the concentration of the present peptide is preferably 20 nM or more and the concentration of the rare earth material is preferably 100 uM (micromolars) or more.

(Mineralization using the Present Peptide)

According to the present peptide, a rare earth-containing inorganic compound can be obtained from the present peptide and a starting material (mineralization starting material) of the rare earth-containing inorganic compound. The rare earth-containing inorganic compound may be crystalline or amorphous when it is produced. When the rare earth-containing inorganic compound is amorphous, it may be converted to a crystal by optionally carrying out a calcination step.

In order to carry out mineralization, the present peptide and a starting material (mineralization starting material) of a rare earth inorganic compound may be incubated in a liquid medium. The mineralization starting material includes a rare earth ion. The rare earth ion may be used in the form that is soluble in a medium used for mineralization such as nitrates and hydrochlorides. The mineralization starting material further includes a constituent material of a rare earth inorganic compound such as oxides, hydroxides and inorganic acids. The constituent material of oxides and hydroxides may exist in an aqueous medium depending on the property of the liquid and the constituent material of inorganic acids may be provided as an anion in an aqueous medium and the like.

The conditions of incubation are not particularly limited as far as they allow the present peptide to exhibit the mineralization activity. Typically, the conditions employed may be those under which the present peptide described hereinabove can exhibit the binding ability to a rare earth material. Because production and deposition of inorganic compounds vary according to pH, temperature and/or incubation period, it is preferable to appropriately adjust pH, temperature and/or incubation period by appropriately extending or shortening the period and the like. For example, the present inventors have confirmed the mineralization activity of the present peptide at pH 5 or higher and 8 or lower and 4 deg C. or higher and 80 deg C. or lower.

During mineralization using the present peptide, the present peptide and the mineralization starting material may be statically incubated or may be stirred at such an extent that the stirring does not inhibit the mineralization. The rare earth-containing inorganic compound resulting from mineralization can be obtained as an insoluble substance (precipitate) in a liquid medium used for incubation. The rare earth-containing inorganic compound can be separated from the present peptide by centrifugation to recover the solid phase and separation of the present peptide using a surfactant and the like. The rare earth inorganic compound can be obtained by further carrying out drying and/or calcination, if necessary.

The concentration of the present peptide and the concentration of the mineralization starting material in the liquid medium in order to allow exhibition of the mineralization activity of the present peptide are again not particularly limited. For example, it is preferable that the concentration of the present peptide is 5 µM or more and the concentration of the mineralization starting material, a rare earth ion, is 100 µM or more.

The concentration of a mineralization starting material of the inorganic compound other than the rare earth may also be similar to the concentration of the rare earth ion.

Incubation of the present peptide for mineralization is advantageous because mineralization can be carried out conveniently under low cost conditions.

Drying of a rare earth-containing inorganic compound obtained from mineralization and calcination of an amorphous rare earth-containing inorganic compound for crystallization are described hereinafter.

(Complex and Production Method thereof)

A complex described herein is a complex of the present peptide and a rare earth material (a rare earth and/or an inorganic compound thereof such as an oxide) (hereinafter also referred to as "present complex"). The present complex includes the present peptide and a rare earth and/or an inorganic compound thereof. The mode of formation of the complex of both substances is not particularly limited. The peptide may be associated with a label substance, a tag, a solid phase support or a biological support described hereinabove. The rare earth may be in the form of ion and/or metal inorganic compound.

The complex may include one type of present peptide bound to two or more types of rare earths or two or more types of present peptides bound to one type of rare earth.

A method for producing the complex may include the step of bringing the present peptide and a rare earth material into contact to form the complex thereof. The complex formation step may be carried out by, as described hereinabove, bringing the present peptide into contact with the rare earth material under the condition under which denaturation of the present peptide is suppressed.

A method for producing the complex may be a method for producing a rare earth-containing inorganic compound described hereinbelow.

Production of the complex is useful for recovery and detection of a rare earth material and identification of a rare earth-binding sequence (screening of the present peptide).

(Method for Recovery of a Rare Earth Material)

A method for recovering a rare earth material as described herein may include the complex formation step described above and the step of recovering the complex. Upon recovery of the complex, separation may be carried out according to the properties of the rare earth material or the complex may be recovered by means of the present peptide. For example, a complex obtained by bringing the present peptide into contact with a resource substance possibly containing a rare earth (various recycle materials such as coal ash and petroleum ash, mineral resources, marine resources) may be recovered by a method depending on the properties of the present peptide per se, a label substance attached to the present peptide or a rare earth material bound to the present peptide. In order to recover the complex by means of the present peptide per se, an antibody specifically recognizing the present peptide may be used. A suitable recovery step may alternatively be carried out depending on a tag in the present peptide. Separation may also be carried out according to the rare earth material in the complex. The complex can be effectively recovered because the present peptide and the rare earth material are used as indices of recovery.

The rare earth material can be recovered from the complex by, for example, denaturing the present peptide in isopropanol or a mixed solution of methanol and acetone (e.g. 1:1) or in a surfactant solution, or bringing the complex into contact with a solvent that blocks an interaction between the present peptide and the rare earth material in order to separate and recover the rare earth from the present peptide. The treatment for eliminating the interaction between the present peptide and the rare earth material in the complex and the extent of elimination may be appropriately selected according to the type of the rare earth material and the binding strength thereof to the present peptide.

(Method for Detecting a Rare Earth Material)

A method for detecting a rare earth material as described herein may include the complex formation step described above and the step of detecting the complex. The complex can be detected according to the properties of a rare earth material or by means of the present peptide. For example, a complex obtained by bringing the present peptide into contact with a resource substance possibly containing a rare earth (various recycle materials such as coal ash and petroleum ash, mineral resources, marine resources) may be detected by a method depending on the properties of the present peptide per se, a label substance attached to the present peptide or a rare earth material bound to the present peptide. In order to detect the rare earth material by means of the present peptide per se, an antibody specifically recognizing the present peptide may be used. A suitable detection step may alternatively be carried out depending on a label substance in the present peptide. Detection may also be carried out according to the rare earth material in the complex. The complex can be reliably detected because the present peptide and the rare earth material are used as indices of detection.

(Method for Screening a Peptide Capable of Binding to a Rare Earth Material)

A method for screening a rare earth-binding peptide as described herein may include the step of bringing a rare earth material into contact with one or more test peptides and evaluating the binding ability of the one or more test peptides to the rare earth material. According to the method of screening of the present disclosure, a peptide having a binding property to a rare earth material can be screened. In other words, a rare earth-binding sequence can be screened or identified.

Examples of a rare earth material include, as described hereinabove, rare earth single substances, rare earth ions and inorganic compounds of rare earths such as oxides. These substances can be independently used as the rare earth material for evaluation of the binding property of a test peptide. When a rare earth ion is used, it may be a solution of a nitrate, a hydrochloride or the like. When a rare earth inorganic compound or a rare earth single substance is used, it may be used in the form of dispersion as it is not soluble.

Examples of the test peptide include, without limitation, peptides having natural amino acid sequences as well as peptides having artificial amino acid sequences. The length of the peptide is not particularly limited. The length may be, as described hereinabove, generally 100 or less amino acid residues, typically preferably 5 or more, more preferably 7 or more and still more preferably 8 or more amino acid residues. The length may be 25 or less, 20 or less or 15 or less amino acid residues. The test peptide may be a cyclic peptide. The cyclic peptide can be formed by means of a disulfide bond between two or more cysteine residues.

The test peptide may be a natural L-form polymer or a non-natural D-form polymer. The test peptide may include an artificial amino acid residue.

The test peptide may be obtained and screened by methods in which various peptides are displayed such as phage display, ribosome display, in vitro virus and the like, by chemical synthesis or genetic engineering synthesis including cell-free protein synthesis and the like. The test peptide may belong to a mutant library prepared based on a certain amino acid sequence by a well-known method. Further, the test peptide may be, as the present peptide, supported on a solid phase support or a biological support.

The test peptide may be attached to, as described hereinabove for the present peptide, a label substance or a tag so as to be convenient for evaluation of the binding property to a rare earth material. When an amino acid sequence of a test peptide is known, an antibody specifically binding to the test peptide may be prepared beforehand. Using the present peptide having such an additive is suitable for secondary screening for further evaluating the binding ability to a rare earth material.

As described hereinabove, a test peptide may be brought into contact with a rare earth material while denaturation of the test peptide is suppressed. Typically, a test peptide is brought into contact with a rare earth material in a solution system.

The mode of contact between one or more rare earth materials and a test peptide is not particularly limited. Particularly in a secondary screening for evaluating the binding ability to the rare earth material(s) with high accuracy, a rare earth material-immobilized solid phase support may be used for example including an array of the rare earth material(s) immobilized on a solid phase support. By using such a rare earth material-immobilized solid phase support, more than one rare earth material and more than one test peptide can be collectively evaluated for the binding ability. The rare earth material-immobilized solid phase support may be, for example, a sheet (plate)-shaped solid phase support including wells in which a rare earth material(s) is immobilized. A rare earth material may be fixed by supplying a dispersion of the rare earth material to a surface such as glass or plastics and drying thereof under vacuum, for example.

A complex obtained by binding of a rare earth material to a test peptide can be identified and recovered by means of the test peptide per se or a label substance attached thereto. A rare earth material and a test peptide that did not form a complex have a mass lower than that of the complex, and thus can be removed as a supernatant or the like according to a separation method utilizing the difference in the mass such as centrifugation, resulting in purification of the complex. In this case, the remaining complex may be added with, as described hereinabove, a surfactant solution and the like to eliminate a complex of the test peptide and the rare earth material due to non-specific binding, again subjected to centrifugation to remove a supernatant and the like, thereby removing the test peptide non-specifically bound to the rare earth material. By repeating such a washing procedure, a test peptide binding to a rare earth material can be screened with high accuracy.

By carrying out more than one set of one or more washing steps after the complex formation step, the test peptide can be concentrated relative to the rare earth material and the test peptide screened can have high binding ability to the rare earth material. It is preferable to repeat the set 3 or more times, more preferably 4 or more times, still more preferably 5 or more times and yet more preferably 6 or more times. The effect of washing can be generally seen up to around 10 times.

By optionally identifying and recovering a complex or a test peptide in a complex and determining the amino acid sequence of the test peptide, a rare earth-binding sequence capable of binding to a rare earth material used can be identified or screened. When the amino acid sequence of the test peptide is unknown such as in phage display, the sequence of the test peptide is analyzed to identify the rare earth-binding sequence.

When carrying out the screening method as primary screening against a particular rare earth material, it is preferable that the method is carried out according to phage display and the like. In this case, repetition of the set as described above corresponds to panning in Examples.

In a secondary screening for evaluating the binding ability of a test peptide to a particular rare earth material or to more than one rare earth material, it is useful for accurate evaluation to use a solid phase support (array, etc.) including a rare earth material immobilized on the solid phase support or the like.

According to the present screening method, a rare earth-binding sequence can be identified and screened that specifically binds to a particular rare earth material or two or more rare earth materials.

(Method for Producing a Rare Earth-containing Inorganic Compound)

According to the present specification, provided is a method for producing a rare earth-containing inorganic compound. The present production method includes the step of bringing a rare earth ion serving as a starting material of the rare earth-containing inorganic compound into contact with another starting material of the rare earth-containing inorganic compound in a liquid medium and in the presence of the present peptide to produce the rare earth-containing inorganic compound. According to the present production method, a rare earth-containing inorganic compound can be readily obtained with low cost.

The conditions for mineralization with the present peptide as described hereinabove can be applied to the rare earth-containing inorganic compound production step.

The present production method can further include a rare earth-containing inorganic compound recovery step. As a rare earth-containing inorganic compound generated is insoluble, the rare earth-containing inorganic compound can be separated and recovered by solid-liquid separation technique. Prior to, during or after solid-liquid separation, binding between a rare earth-containing inorganic compound and the present peptide may be removed by denaturation or the like of the present peptide in order to recover the rare earth-containing inorganic compound that is not forming a complex.

The present production method may further include a drying step of the recovered rare earth-containing inorganic compound. The drying step may be a general drying step without limitation.

The present production method may further include a calcination step of the recovered rare earth-containing inorganic compound. The calcination step can be carried out in order to promote crystallization of an amorphous rare earth-containing inorganic compound, for example. Alternatively the calcination step can be carried out in order to convert a hydroxide to an oxide by dehydration.

The calcination step for crystallization can be carried out based on the conditions for crystallization of well-known amorphous compounds. The calcination step may be, for example, carried out at 300 deg C. or higher and 1500 deg C. or lower. When the rare earth-containing inorganic compound obtained by mineralization is an inorganic salt such as a carbonate, the heating temperature used may be the one at which the inorganic salt is crystallized while maintaining the status of the inorganic salt. When an oxide is obtained by eliminating an inorganic acid such as decarbonation, the temperature selected may be the one at which the elimination occurs, as appropriate.

The present production method is also advantageous in that particles of the rare earth-containing inorganic compound having the size of the order of nm can be produced. The present production method may also serve as a method for producing a complex of the present peptide and a rare earth-containing inorganic compound.

EXAMPLES

The disclosure herein is specifically explained by way of Examples which do not limit the present invention.

Example 1

(Construction of Random Peptide-displaying T7 Phage Library)

PCR reaction was carried out using two oligonucleotide primers: T7-Libup (ATG ATT ACC AGG ATC CGA ATT CAG GTG GAG GTT CG; SEQ ID NO: 30) and T7-Libdownt (ACT ATC GTC GGC CGC AAG CTT TTA GCT; SEQ ID NO: 31) to amplify a template DNA (CGA ATT CAG GTG GAG GTT CGT GT(NNK)$_{9-12}$ TGT AGC TAA AAG CTT GCG GCC GA; SEQ ID NO: 32).

N=A: 25%, T: 25%, G: 25%, C: 25% (mixed base of A/T/G/C at equal amounts)

K=mixed base of A: 0%, T: 50%, G: 50%, C: 0%

The amplified DNA fragments were subjected to phenol treatment and butanol concentration according to conventional protocols, followed by purification with the QIAquick PCR Purification kit (QIAGEN). Purified DNAs were treated with restriction enzymes Hind III and Eco RI (TaKaRa Bio Inc.) and ligated to the T7select 10-3 vector arms (Novagen) to construct T7 phage genomes.

The constructed phage genomes were mixed with the T7select packaging solution (Novagen) to construct T7 phages having random peptide-introduced T7 genomic DNA. The obtained phages was sampled and counted for the phage population. It was found that the phage library constructed had a sequence diversity of $1.0 \times 10^6$ to $4.0 \times 10^7$.

After amplifying the constructed phage population by infection of E. coli BLT5403 which was cultured until $OD_{660nm}$=0.6 to 1.0, the phages were concentrated and purified by passing the phages through a 0.22 um (micrometers) filter in 8% polyethylene glycol. The number of phages was counted after purification, from which it was found that each library contained about $1.0 \times 10^{12}$ pfu/ml of phages and one peptide phage was amplified by 100,000 to 1,000,000 times.

Example 2

(Biopanning against Dysprosium Oxide using Random Peptide-displaying T7 Phage Library)

Using the random peptide-displaying T7 phage library prepared in Example 1, it was sought to isolate T7 phages displaying peptides binding to dysprosium oxide. The scheme is shown in FIG. 1.

Dysprosium oxide (Sigma-Aldrich) was washed in a mixed solution of methanol and acetone (1:1), then washed in isopropanol and dispersed in TBS.

The dispersion containing 500 ug (micrograms) of dysprosium oxide and the T7 phage library were mixed and the reaction was allowed to proceed for 1 hour at room temperature. Thereafter particles were precipitated by centrifugation (6000 rpm, 3 minutes) and the supernatant was removed, thereby removing unbound phage.

After removing the supernatant, the precipitate was added with TBST to disperse dysprosium oxide. The dispersion was again centrifuged in order to remove the phages non-specifically binding to the particles. By repeating the procedure (washing procedure) 3 to 10 times, peptide phages non-specifically binding to dysprosium oxide were removed.

After removing unbound phages and non-specifically binding phages by washing, the remaining phages were mixed with a solution (10 ml) of E. coli BLT 5403 cultured until $OD_{660nm}$=0.6 to 1.0 and incubated at 37 deg C. until complete lysis of E. coli.

After complete lysis of E. coli, 5 M NaCl was added in an amount of 1/10 of the culture medium, the mixture was centrifuged (3500 rpm, 15 minutes) to precipitate the insoluble fraction including cell walls of E. coli and the like and the supernatant was recovered.

A solution of 50% polyethylene glycol 6000 was added in an amount of ⅙ of the recovered supernatant, and the mixture was stirred and centrifuged at 3500 rpm for 15 minutes to precipitate T7 phages. The precipitated T7 phage population was dissolved in a TBS solution, subjected to the filtering treatment through a 0.22 um filter and stored at 4 deg C. until use.

Example 3

(Confirmation of Dysprosium Oxide-binding Phage Concentrated by Biopanning)

After repeating the series of procedures described in Example 2 5 times, the number of phages binding to dysprosium oxide was determined after each cycle of the procedures.

First of all, dysprosium oxide was washed in a mixed solution of methanol and acetone (1:1), washed in isopropanol and dispersed in TBS.

The dispersion containing 500 ug of dysprosium oxide was mixed with pooled phages after each cycle and the reaction was allowed to proceed for 1 hour at room temperature. Thereafter the reaction solution was centrifuged (6000 rpm, 3 minutes) and the supernatant was removed. The precipitate was washed in TBST 10 times.

After washing, the number of phages binding to dysprosium oxide particles was determined by plaque assay. The results are shown in FIG. 2. As shown in FIG. 2, the number of phages binding to dysprosium oxide particles was increased with the progress of panning From these results, it was found that the repetition of panning allows screening of peptide-displaying phages having excellent binding ability to dysprosium oxide.

Example 4

The pooled phage after 5 cycles of panning was used to obtain monoclones of phages, and randomly-selected 35 kinds of phages were subjected to the analysis of peptide sequences displayed thereby. As a result, 31 different sequences were confirmed. Representative 7 different amino acid sequences are shown hereinbelow.

TABLE 1

Amino acid sequences analysis of peptides displayed on the monoclonal phages

| No. | Sequence | Frequency |
|---|---|---|
| 9-4 (LOB1) | SCLYPSWSDYAFCS* | 4/35 |
| 9-5 | SCAYPSELLHRGCS* | 1/35 |
| 9-6 | SCCWQVARGLGKSRCS* | 1/35 |
| 9-18 | SCCLVPAESRTRSRCS* | 1/35 |
| 10-4 | SCVKGEFFRSISTCS* | 1/35 |
| 10-9 | SCVCAGSARSWSMCN* | 1/35 |
| 10-20 (LOB2) | SCLWGDVSELDFLCS* | 2/35 |

As shown in Table 1, sequences 9-4 (LOB 1) and 10-20 (LOB2) were found in 4 and 2 clones, respectively, and were free from basic amino acids (K, R and H) unlike other amino acid sequences.

Example 5

(Screening of Monoclonal Phage Displaying Peptide Binding to Dysprosium Oxide)

Among peptide phages identified in Example 4, phage clones having characteristic sequences shown in Table 1 were evaluated for binding ability to dysprosium oxide.

Dysprosium oxide (500 ug) washed and dispersed in TBS was mixed with each phage and the reaction was allowed to proceed for 1 hour at room temperature. Thereafter the reaction solution was centrifuged (6000 rpm, 3 minutes) and the supernatant was removed. The precipitate was washed in TBST 10 times. After washing, the number of phages bound to dysprosium oxide particles were determined by plaque assay. The results are shown in FIG. 3. As shown in FIG. 3, the number of bound phages was about 100 times higher than that of the wild type for the sequences 9-4 (LOB1) and 10-20 (LOB2) which were redundant.

Example 6

(Preparation of Synthetic Peptides)

The peptides displayed by phages, LOB 1 and LOB2, which bound to dysprosium oxide were synthesized by Fmoc solid-phase synthesis. The synthesized peptides were biotinylated at the N-terminal via GGG derived from g10 sequence.

Each peptide was cleaved from the resin and deprotected and an intramolecular disulfide bond was formed using an appropriate oxidizing agent such as iodine. The peptide was then purified by reverse-phase HPLC and lyophilized.

Example 7

(Evaluation of Binding of Synthetic Peptides and Dysprosium Oxide)

The synthetic peptide (LOB2) prepared in Example 6 was evaluated for binding thereof to dysprosium oxide immobilized on a microplate.

Dysprosium oxide (5 ug) was washed, dispersed in isopropanol, added to a microplate and dried under vacuum for 1 hour.

The microplate after drying and immobilization was washed with ultrapure water, incubated with 400 ul (microliters) of 0.5% BSA at room temperature for 90 minutes for blocking and washed 3 times with TBST.

The synthetic peptide LOB2 (final concentration: 80 nM) was mixed with SA-HRP (final concentration: 20 nM) to allow reaction for 10 minutes and the mixture was washed 5 times with TBST.

After washing of the microplate, a TMB solution was added to each well. After confirming some extent of color generation, 1 N HCl was added to each well to terminate the reaction and the absorbance at 450 nm was determined on the microplate reader Spectra max plus 384. Thereby the binding ability of the synthetic peptide to dysprosium oxide particles was evaluated. A negative control used was a lanthanoid ion-binding peptide (La-BP, amino acid sequence: GGGS-FIDTNNDGDWIEGDELLA, SEQ ID NO: 38). The results are shown in FIG. 4.

As shown in FIG. 4, the LOB2 showed the binding ability specific to dysprosium oxide in a concentration dependent manner.

Example 8

(Evaluation of Binding Specificity of Synthetic Peptides)

In the same manner as in Example 7, synthetic peptides LOB 1 and LOB2 and rare earth metal oxide particles ($La_2O_3$, $CeO_2$, $Nd_2O_3$, $Sm_2O_3$, $Gd_2O_3$, $Tb_4O_7$, $Dy_2O_3$, $Ho_2O_3$, $Er_2O_3$, $Yb_2O_3$, $Y_2O_3$, $TiO_2$, hydroxyapatite and Ag)

immobilized on microplates were generally evaluated. The results for LOB 1 and LOB2 are shown in FIGS. 6 and 5, respectively.

As shown in FIG. 5, LOB2 had high binding ability to $La_2O_3$, $CeO_2$, $Nd_2O_3$, $Sm_2O_3$, $Gd_2O_3$, $Dy_2O_3$, $Ho_2O_3$ and $Er_2O_3$. Among others, LOB2 showed high binding ability to $CeO_2$, $Nd_2O_3$, $Gd_2O_3$ and $Dy_2O_3$, further showed high binding ability to $CeO_2$ and $Nd_2O_3$ and showed the highest binding ability to $Nd_2O_3$. La-BP showed little binding to $La_2O_3$ and some binding to $CeO_2$ of which extent was incomparable to the binding ability of LOB2.

As shown in FIG. 6, LOB 1 had high binding ability to $La_2O_3$, $CeO_2$, $Nd_2O_3$, $Sm_2O_3$, $Gd_2O_3$, $Tb_4O_7$, $Dy_2O_3$, $Ho_2O_3$ and $Er_2O_3$. Among others, LOB 1 showed high binding ability to $CeO_2$, $Nd_2O_3$, $Gd_2O_3$ and $Dy_2O_3$, further showed high binding ability to $La_2O_3$, $CeO_2$ and $Ho_2O_3$ and showed the highest binding ability to $La_2O_3$ and $CeO_2$.

According to the above results, it was found that synthetic peptides LOB1 and LOB2 had binding ability to more than one oxides of rare earths belonging to the lanthanoid series, while respectively showed distinct binding specificity to the oxides.

Example 9

(Alanine Substitution Test of LOB2 Peptide)

T7 phages displaying peptide sequences which were alanine substituents at each amino acid position in the amino acid sequence of the LOB2 peptide were prepared in the same manner as in Example 1 using the T7-Libup and T7-Libdown indicated in Example 1 and oligonucleotide primers shown in Table 2. Peptide sequences displayed by prepared phages are shown in FIG. 7.

The prepared LOB2-ala substituent phages were evaluated for binding to $Dy_2O_3$ in the same manner as in Example 7. The results are shown in FIG. 8.

As shown in FIG. 8, substitutions to alanine at positions 3, 4, 10 and 12 to 14 significantly affected and the amount of binding was significantly decreased. Substitutions to alanine at positions 2, 6 and 9 also significantly affected. Based on the above, it was found that the positions 3, 4, 10 and 12 to 14 are preferably leucine, tryptophan, leucine, phenylalanine, leucine and cysteine, respectively. It was also found that the positions 2, 6 and 9 are preferably cysteine, aspartic acid and glutamic acid, respectively.

Example 10

(Construction of Partial Mutant Library)

After the LOB1 and LOB2, peptide libraries of 14 or 15 residues were prepared which displayed sequences having fixed amino acids of Ser and Cis at positions 1 and 2 and Cis and Ser at positions 13 and 14 or 14 and 15, with other positions having amino acids derived from the dysprosium oxide-binding peptides at the probability of about 30%.

Partial mutant libraries were prepared in the same manner as in Example 1 using two types of DNA templates (LOB1-2nd and LOB2-2nd).

LOB1-2nd:

(SEQ ID NO: 54)
CGA ATT CAG GTG GAG GTT CGT GTN JFJ OOE ONO FNE
JNF ONO FNN JFO FNJ JNN JFT GTA GCT AAA AGC TTG
CGG CCG A

TABLE 2

Primers for constructing alanine substitution phages

| Oligo Name | Sequence (5' to 3') |
|---|---|
| 1SA | AGGATCCGAATTCAGGTGGAGGTGCATGTTTGTGGGGTGAT |
| 2CA | ATCCGAATTCAGGTGGAGGTTCGGCATTGTGGGGTGATGTT |
| 3LA | ATCCGAATTCAGGTGGAGGTTCGTGTGCATGGGGTGATGTTAGT |
| 4WA | ATCCGAATTCAGGTGGAGGTTCGTGTTTGGCAGGTGATGTTAGTGAG |
| 5GA | ATCCGAATTCAGGTGGAGGTTCGTGTTTGTGGGCAGATGTTAGTGAGCTG |
| 6DA | ATCCGAATTCAGGTGGAGGTTCGTGTTTGTGGGGTGCAGTTAGTGAGCTGGAT |
| 7VA | ATCCGAATTCAGGTGGAGGTTCGTGTTTGTGGGGTGATGCAAGTGAGCTGGATTTT |
| 8SA-rc | TCGGCCGCAAGCTTTTAGCTACACAGAAAATCCAGCTCTGCAACATCACCCCACAA |
| 9EA-rc | TCGGCCGCAAGCTTTTAGCTACACAGAAAATCCAGTGCACTAACATCACCCCA |
| 10LA-rc | TCGGCCGCAAGCTTTTAGCTACACAGAAAATCTGCCTCACTAACATCACC |
| 11DA-rc | TCGGCCGCAAGCTTTTAGCTACACAGAAATGCCAGCTCACTAACATC |
| 12FA-rc | TCGGCCGCAAGCTTTTAGCTACACAGTGCATCCAGCTCACTAAC |
| 13LA-rc | TCGGCCGCAAGCTTTTAGCTACATGCAAAATCCAGCTCACT |
| 14CA-rc | TCGGCCGCAAGCTTTTAGCTTGCCAGAAAATCCAGCTC |
| 15SA-rc | TCGGCCGCAAGCTTTTATGCACACAGAAAATCCAG |

-continued

LOB2-2nd:
(SEQ ID NO: 55)
CGA ATT CAG GTG GAG GTT CGT GTN JFJ OOE ONO FNE
JNF ONO FNN JFO FNJ JNN JFT GTA GCT AAA AGC TTG
CGG CCG A

In two DNA templates, F, J, O, X, N, B, E and P respectively represent DNA sequences randomly synthesized so as to have the base sequences biased as follows:

F=mixed base of A: 70%, T: 10%, G: 10%, C: 10%
J=mixed base of A: 10%, T: 70%, G: 10%, C: 10%
O=mixed base of A: 10%, T: 10%, G: 70%, C: 10%
X=mixed base of A: 10%, T: 10%, G: 10%, C: 70%
N=mixed base of A, T, G and C at equal amounts
B=mixed base of T, G and C at equal amounts
E=mixed base of A: 20%, T: 20%, G: 40%, C: 20%
P=mixed base of A: 20%, T: 20%, G: 20%, C: 40%

The constructed phage populations were counted and it was confirmed that the LOB1 partial mutant library had a diversity of $3.0 \times 10^7$ and the LOB2 partial mutant library had a diversity of $8.0 \times 10^7$.

Example 11

(Biopanning using Partial Mutant Libraries and Sequence Analysis of Peptides Displayed by Isolated Phages)

In the same manner as in Example 2, the partial mutant libraries prepared in Example 10 were subjected to biopanning against dysprosium oxide 5 times. Thereafter, obtained pooled phages were used to obtain monoclones, and analyzed for amino acid sequence of the displayed peptides in the same manner as Example 4. The amino acid sequences of peptides displayed by phage clones in the LOB2 and LOB 1 libraries are shown in FIGS. 9 and 10, respectively.

As shown in FIG. 9, in the partial mutant library of the LOB2 peptide, there was a tendency to maintain acidic amino acid residues originally contained in the LOB2. Among others, the acidic amino acid residue (glutamic acid) at the residue 9 was maintained as glutamic acid or aspartic acid in 10 clones among 11. In addition, the acidic amino acid residue (aspartic acid) at the residue 11 was maintained as aspartic acid or glutamic acid in 6 clones among 11. The acidic amino acid residue (aspartic acid) at the residues 6 was also maintained as aspartic acid or glutamic acid in 5 clones among 11. There was also a tendency to maintain the properties (neutral amino acid, acidic amino acid, basic amino acid, aromatic amino acid, cyclic amino acid, sulfur-containing amino acid, acid amide amino acid) of amino acid residues in the LOB2 peptide at other positions.

As shown in FIG. 10, in the partial mutant library of the LOB 1 peptide, there was a tendency to maintain the acidic amino acid residue originally contained in the LOB 1. Namely, the acidic amino acid residue (glutamic acid) at the residue 9 was maintained as glutamic acid or aspartic acid in all clones (14 clones). There was also a tendency to maintain the properties (neutral amino acid, acidic amino acid, basic amino acid, aromatic amino acid, cyclic amino acid, sulfur-containing amino acid, acid amide amino acid) of amino acid residues in the LOB 1 peptide at other positions.

(Evaluation of Mineralization Activity of LOB2 Peptide)

Binding of the LOB2 peptide to dysprosium ion was evaluated. In a HEPES buffer (HEPES 1 mM, pH 6.2), dysprosium nitrate (dysprosium was present as an ion) and the peptide dissolved in DMSO were diluted so as to be 1 mM and 10 uM (DMSO 5%) respectively, and an Eppendorf tube containing the diluted solution was statically incubated under room temperature.

After 5 hours, the tube was centrifuged at 15000 rpm for 10 minutes, the supernatant was removed and 100 ul of ultrapure water was then added to the tube to wash the precipitate by shaking. After repeating such centrifugation and washing by shaking twice, the precipitate was thoroughly dispersed in 20 ul of ultrapure water and subjected to analysis by TEM and EDX (Hitachi High Technologies Corporation). The results are shown in FIGS. 11 and 12.

As shown in FIG. 11, it was confirmed by TEM analysis that some particles were produced by bringing the LOB2 peptide into contact with dysprosium ion. As shown in FIG. 12, it was found by EDX analysis that the produced particles contained dysprosium.

According to the above results, it was found that the LOB2 peptide is capable of binding to dysprosium oxide and precipitating dysprosium inorganic compound from dysprosium ion.

Example 12

(Effect of Incubation pH on Mineralization Activity of LOB2 Peptide)

In a HEPS buffer (HEPES 1 mM, pH 7.5), the LOB2 peptide was diluted so as to be 10 uM (DMSO 3%), pH was adjusted to 3.9 to 8.0 with 0.1 N HCl or 0.1 M NaOH, dysprosium ion as dysprosium nitrate was added and the solutions were incubated under room temperature while shaking.

After 5 hours of incubation, each solution was centrifuged at 15000 rpm for 10 minutes, the supernatant was removed and 100 ul of ultrapure water was then added to the tube to wash the precipitate by shaking. After repeating such centrifugation and washing by shaking twice, the precipitate was dispersed in 20 ul of ultrapure water, 10 ul of the dispersion was dropped on a carbon tape which was then left in a clean bench until dryness and analyzed by SEM/EDX. The results are shown in FIGS. 13A and 13B.

As shown in FIGS. 13A and 13B, it was found that the mineralization activity was exhibited in a wide range of pH, resulting in production of dysprosium inorganic compound. In the present Example, preferable mineralization was confirmed in the range of pH 5.0 or higher and pH 8.0 or lower.

Example 13

(Effect of Reaction Temperature on Mineralization Activity of LOB2 Peptide)

In a HEPS buffer (HEPES 1 mM, pH 7.5), the LOB2 peptide was diluted so as to be 10 uM (DMSO 3%), dysprosium ion as dysprosium nitrate was added and the solutions were statically incubated under 4 deg C., 10 deg C., 20 deg C., 30 deg C., 40 deg C., 50 deg C., 60 deg C. and 80 deg C.

After 5 hours of incubation, each solution was centrifuged and washed by stirring in the same manner as in Example 12 and the precipitate finally obtained was subjected to analysis by SEM/EDX. The results are shown in FIGS. 14A and 14B.

As shown in FIGS. 14A and 14B, it was found that the mineralization activity was exhibited in a wide range of temperature, resulting in production of dysprosium oxide. In the present Example, preferable mineralization was confirmed in the range of 4 deg C. or higher and 8 or lower.

Example 14

(Particle Diameter of Particles Produced by Mineralization Activity of LOB2 Peptide)

In a HEPS buffer (HEPES 1 mM, pH 7.5), the LOB2 peptide was diluted so as to be 10 uM (DMSO 3%), dysprosium ion as dysprosium nitrate was added and the solution was incubated under room temperature for 5 hours while shaking.

After 5 hours, the solution was centrifuged and washed by stirring in the same manner as in Example 12 and the precipitate finally obtained was subjected to analysis by TEM. The result is shown in FIG. 15.

As shown in FIG. 15, the resulting dysprosium inorganic compound particles generally had 5 nm or less, confirming obtainment of particles of the order of nanometers.

SEQUENCE LISTING FREE TEXT

SEQ ID NOs: 1-29, 33-38: synthetic peptides
SEQ ID NOs: 30-32, 39-55: synthetic nucleotides

The invention claimed is:

1. A method for producing a complex of a rare earth material-binding agent and a rare earth material, comprising:
    bringing the rare earth material-binding agent comprising a peptide capable of binding to the rare earth material into contact with the rare earth material to form the complex,
    wherein
    the rare earth material comprises at least one rare earth atom selected from the group consisting of lanthanum (La), lanthanum (La) ion, cerium (Ce), cerium (Ce) ion, neodymium (Nd), neodymium (Nd) ion, samarium (Sm), samarium (Sm) ion, gadolinium (Gd), gadolinium (Gd) ion, terbium (Tb), terbium (Tb) ion, dysprosium (Dy), dysprosium (Dy) ion, holmium (Ho), holmium (Ho) ion, erbium (Er), and erbium (Er) ion, and
    the peptide has an amino acid sequence represented by Leu-Trp-Gly-Asp/Glu-Val-Ser/Asn-Asp/Glu-Leu/Val-Asp/Glu-Phe/Leu-Leu.

2. The method according to claim 1, wherein the peptide is a cyclic peptide.

3. The method according to claim 1, wherein the rare earth material comprises dysprosium and a dysprosium ion, and the binding agent binds to the dysprosium ion and an oxide of dysprosium.

4. The method according to claim 1, wherein the peptide has a label substance bound thereto.

5. The method according to claim 1, wherein the rare earth atom is at least one rare earth ion selected from the group consisting of lanthanum (La) ion, cerium (Ce) ion, neodymium (Nd) ion, samarium (Sm) ion, gadolinium (Gd) ion, terbium (Tb) ion, dysprosium (Dy) ion, holmium (Ho) ion, and erbium (Er) ion.

6. The method according to claim 5, wherein the complex is an inorganic compound comprising the at least one rare earth ion.

7. The method according to claim 5, wherein the at least one rare earth ion is dysprosium (Dy) ion.

8. The method according to claim 6, wherein the at least one rare earth ion is dysprosium (Dy) ion.

* * * * *

```
                        SEQUENCE LISTING

<160> NUMBER OF SEQ ID NOS: 55

<210> SEQ ID NO 1
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(11)
<223> OTHER INFORMATION: Xaa can be any naturally occurring amino acid

<400> SEQUENCE: 1

Xaa Xaa Xaa Xaa Xaa Xaa Xaa Xaa Xaa Xaa Xaa
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(10)
<223> OTHER INFORMATION: Xaa can be any naturally occurring amino acid

<400> SEQUENCE: 2

Xaa Xaa Xaa Xaa Xaa Xaa Xaa Xaa Xaa Xaa
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Ser Cys Leu Trp Gly Asp Val Ser Glu Leu Asp Phe Leu Cys Ser
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic peptide

<400> SEQUENCE: 4

Ser Cys Leu Trp Ile Glu Ser Leu Asp Leu Asp Gly Leu Cys Ser
1               5                   10                  15

<210> SEQ ID NO 5
<211> LENGTH: 15
```

```
<212> TYPE: PRT
<213> ORGANISM: Artificial
<220> FEATURE:
<223> OTHER INFORMATION: Synthetic peptide

<400> SEQUENCE: 5

Ser Cys Leu Cys Cys Glu Val Ser Asp Leu Gly Leu Val Cys Ser
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

Ser Cys Val Cys Ile Glu Arg Arg Glu Leu Asp Leu Leu Cys Ser
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic peptide

<400> SEQUENCE: 7

Ser Cys Ile Asp Ser Tyr Val Gly Glu Leu Glu Thr Leu Cys Ser
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Ser Cys Leu Trp Arg Ala Val Cys Asp Leu Gly Ile Glu Cys Ser
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Ser Cys Leu Gly Gly Asp Met Ser Asp Lys Pro Val Ser Cys Ser
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Ser Cys Thr Cys Gly Met Val Asn Asp Val Asp Leu Thr Cys Ser
1               5                   10                  15

<210> SEQ ID NO 11
<211> LENGTH: 15
<212> TYPE: PRT
```

```
<213> ORGANISM: Artificial
<220> FEATURE:
<223> OTHER INFORMATION: Synthetic peptide

<400> SEQUENCE: 11

Ser Cys Ile Val Gly Glu Val Arg Leu Ser Asp Leu Val Cys Ser
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Ser Cys Thr Cys Gly Met Val Asn Asp Val Asp Leu Thr Cys Ser
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Ser Cys Val Trp Arg Gly Phe Lys Asp Gly Gln Trp Phe Cys Ser
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic peptide

<400> SEQUENCE: 14

Ser Cys Val Cys Arg Gly Leu Arg Asp Leu Ala His Asn Cys Ser
1               5                   10                  15

<210> SEQ ID NO 15
<211> LENGTH: 14
<212> TYPE: PRT
<213> ORGANISM: Artificial
<220> FEATURE:
<223> OTHER INFORMATION: Synthetic peptide

<400> SEQUENCE: 15

Ser Cys Leu Tyr Pro Ser Trp Ser Asp Tyr Ala Phe Cys Ser
1               5                   10

<210> SEQ ID NO 16
<211> LENGTH: 14
<212> TYPE: PRT
<213> ORGANISM: Artificial
<220> FEATURE:
<223> OTHER INFORMATION: Synthetic peptide

<400> SEQUENCE: 16

Ser Cys Thr Asp Pro Ser Trp Gly Glu Tyr Gly Phe Cys Ser
1               5                   10

<210> SEQ ID NO 17
<211> LENGTH: 14
<212> TYPE: PRT
<213> ORGANISM: Artificial
```

```
<220> FEATURE:
<223> OTHER INFORMATION: Synthetic peptide

<400> SEQUENCE: 17

Ser Cys Glu Tyr Ser Ser Ala Ser Glu Tyr Ala Arg Cys Ser
1               5                   10

<210> SEQ ID NO 18
<211> LENGTH: 14
<212> TYPE: PRT
<213> ORGANISM: Artificial
<220> FEATURE:
<223> OTHER INFORMATION: Synthetic peptide

<400> SEQUENCE: 18

Ser Cys Ile Tyr Gly Glu Trp Arg Asp Tyr Ala Phe Cys Ser
1               5                   10

<210> SEQ ID NO 19
<211> LENGTH: 14
<212> TYPE: PRT
<213> ORGANISM: Artificial
<220> FEATURE:
<223> OTHER INFORMATION: Synthetic peptide

<400> SEQUENCE: 19

Ser Cys Val Tyr Leu Ser Gly Ser Glu Cys Thr Phe Cys Ser
1               5                   10

<210> SEQ ID NO 20
<211> LENGTH: 14
<212> TYPE: PRT
<213> ORGANISM: Artificial
<220> FEATURE:
<223> OTHER INFORMATION: Synthetic peptide

<400> SEQUENCE: 20

Ser Cys Leu Asn Ala Arg Trp Ser Asp Ser Pro Val Cys Ser
1               5                   10

<210> SEQ ID NO 21
<211> LENGTH: 14
<212> TYPE: PRT
<213> ORGANISM: Artificial
<220> FEATURE:
<223> OTHER INFORMATION: Synthetic peptide

<400> SEQUENCE: 21

Ser Cys Leu Asn Thr Ile Trp Ala Asp Tyr Gly Leu Cys Ser
1               5                   10

<210> SEQ ID NO 22
<211> LENGTH: 14
<212> TYPE: PRT
<213> ORGANISM: Artificial
<220> FEATURE:
<223> OTHER INFORMATION: Synthetic peptide

<400> SEQUENCE: 22

Ser Cys Lys Asp Val Ser Trp Gly Asp Ile Ala Cys Cys Ser
1               5                   10

<210> SEQ ID NO 23
<211> LENGTH: 14
<212> TYPE: PRT
<213> ORGANISM: Artificial
<220> FEATURE:
```

<223> OTHER INFORMATION: Synthetic peptide

<400> SEQUENCE: 23

Ser Cys Phe Glu Phe Ser Trp Ser Glu Asp Cys Ala Cys Ser
1               5                   10

<210> SEQ ID NO 24
<211> LENGTH: 14
<212> TYPE: PRT
<213> ORGANISM: Artificial
<220> FEATURE:
<223> OTHER INFORMATION: Synthetic peptide

<400> SEQUENCE: 24

Ser Cys Glu Arg Gly Ser Trp Cys Glu Asp Ala Cys Cys Ser
1               5                   10

<210> SEQ ID NO 25
<211> LENGTH: 14
<212> TYPE: PRT
<213> ORGANISM: Artificial
<220> FEATURE:
<223> OTHER INFORMATION: Synthetic peptide

<400> SEQUENCE: 25

Ser Cys Val Tyr Thr Gly Trp Arg Glu Asp Ala Ser Cys Ser
1               5                   10

<210> SEQ ID NO 26
<211> LENGTH: 14
<212> TYPE: PRT
<213> ORGANISM: Artificial
<220> FEATURE:
<223> OTHER INFORMATION: Synthetic peptide

<400> SEQUENCE: 26

Ser Cys Cys Phe Ala Ser Cys Thr Asp Ser Ala Leu Cys Ser
1               5                   10

<210> SEQ ID NO 27
<211> LENGTH: 14
<212> TYPE: PRT
<213> ORGANISM: Artificial
<220> FEATURE:
<223> OTHER INFORMATION: Synthetic peptide

<400> SEQUENCE: 27

Ser Cys Thr Arg Ser Arg Cys Gly Asp Gly Ala Phe Cys Ser
1               5                   10

<210> SEQ ID NO 28
<211> LENGTH: 14
<212> TYPE: PRT
<213> ORGANISM: Artificial
<220> FEATURE:
<223> OTHER INFORMATION: Synthetic peptide

<400> SEQUENCE: 28

Ser Cys Tyr Val Ala Ile Met Ser Glu Lys Ser Phe Cys Ser
1               5                   10

<210> SEQ ID NO 29
<211> LENGTH: 14
<212> TYPE: PRT
<213> ORGANISM: Artificial
<220> FEATURE:
<223> OTHER INFORMATION: Synthetic peptide

<400> SEQUENCE: 29

Ser Cys Ile Glu Ala Arg Tyr Thr Asp His Ala Leu Cys Ser
1               5                   10

<210> SEQ ID NO 30
<211> LENGTH: 35
<212> TYPE: DNA
<213> ORGANISM: Artificial
<220> FEATURE:
<223> OTHER INFORMATION: Synthetic nucleotide

<400> SEQUENCE: 30
atgattacca ggatccgaat tcaggtggag gttcg                                  35

<210> SEQ ID NO 31
<211> LENGTH: 27
<212> TYPE: DNA
<213> ORGANISM: Artificial
<220> FEATURE:
<223> OTHER INFORMATION: Synthetic nucleotide

<400> SEQUENCE: 31
actatcgtcg gccgcaagct tttagct                                           27

<210> SEQ ID NO 32
<211> LENGTH: 47
<212> TYPE: DNA
<213> ORGANISM: Artificial
<220> FEATURE:
<223> OTHER INFORMATION: Synthetic nucleotide
<220> FEATURE:
<221> NAME/KEY: misc_structure
<222> LOCATION: (24)..(24)
<223> OTHER INFORMATION: n is modified as (NNK)9-12, in which N can be
      A, T, G, or C and K can be T or G.
<220> FEATURE:
<221> NAME/KEY: misc_feature
<222> LOCATION: (24)..(24)
<223> OTHER INFORMATION: n is a, c, g, or t

<400> SEQUENCE: 32
cgaattcagg tggaggttcg tgtntgtagc taaaagcttg cggccga                     47

<210> SEQ ID NO 33
<211> LENGTH: 14
<212> TYPE: PRT
<213> ORGANISM: Artificial
<220> FEATURE:
<223> OTHER INFORMATION: Synthetic peptide

<400> SEQUENCE: 33

Ser Cys Ala Tyr Pro Ser Glu Leu Leu His Arg Gly Cys Ser
1               5                   10

<210> SEQ ID NO 34
<211> LENGTH: 16
<212> TYPE: PRT
<213> ORGANISM: Artificial
<220> FEATURE:
<223> OTHER INFORMATION: Synthetic peptide

<400> SEQUENCE: 34

Ser Cys Cys Trp Gln Val Ala Arg Gly Leu Gly Lys Ser Arg Cys Ser
1               5                   10                  15

<210> SEQ ID NO 35

```
<211> LENGTH: 16
<212> TYPE: PRT
<213> ORGANISM: Artificial
<220> FEATURE:
<223> OTHER INFORMATION: Synthetic peptide

<400> SEQUENCE: 35

Ser Cys Cys Leu Val Pro Ala Glu Ser Arg Thr Arg Ser Arg Cys Ser
1               5                   10                  15

<210> SEQ ID NO 36
<211> LENGTH: 15
<212> TYPE: PRT
<213> ORGANISM: Artificial
<220> FEATURE:
<223> OTHER INFORMATION: Synthetic peptide

<400> SEQUENCE: 36

Ser Cys Val Lys Gly Glu Phe Phe Arg Ser Ile Ser Thr Cys Ser
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic peptide

<400> SEQUENCE: 37

Ser Cys Val Cys Ala Gly Ser Ala Arg Ser Trp Ser Met Cys Asn
1               5                   10                  15

<210> SEQ ID NO 38
<211> LENGTH: 22
<212> TYPE: PRT
<213> ORGANISM: Artificial
<220> FEATURE:
<223> OTHER INFORMATION: Synthetic peptide

<400> SEQUENCE: 38

Gly Gly Gly Ser Phe Ile Asp Thr Asn Asn Asp Gly Asp Trp Ile Glu
1               5                   10                  15

Gly Asp Glu Leu Leu Ala
            20

<210> SEQ ID NO 39
<211> LENGTH: 41
<212> TYPE: DNA
<213> ORGANISM: Artificial
<220> FEATURE:
<223> OTHER INFORMATION: Synthetic nucleotide

<400> SEQUENCE: 39
aggatccgaa ttcaggtgga ggtgcatgtt tgtggggtga t                    41

<210> SEQ ID NO 40
<211> LENGTH: 41
<212> TYPE: DNA
<213> ORGANISM: Artificial
<220> FEATURE:
<223> OTHER INFORMATION: Synthetic nucleotide

<400> SEQUENCE: 40
atccgaattc aggtggaggt tcggcattgt ggggtgatgt t                    41

<210> SEQ ID NO 41
```

<211> LENGTH: 44
<212> TYPE: DNA
<213> ORGANISM: Artificial
<220> FEATURE:
<223> OTHER INFORMATION: Synthetic nucleotide

<400> SEQUENCE: 41
atccgaattc aggtggaggt tcgtgtgcat ggggtgatgt tagt            44

<210> SEQ ID NO 42
<211> LENGTH: 47
<212> TYPE: DNA
<213> ORGANISM: Artificial
<220> FEATURE:
<223> OTHER INFORMATION: Synthetic nucleotide

<400> SEQUENCE: 42
atccgaattc aggtggaggt tcgtgtttgg caggtgatgt tagtgag         47

<210> SEQ ID NO 43
<211> LENGTH: 50
<212> TYPE: DNA
<213> ORGANISM: Artificial
<220> FEATURE:
<223> OTHER INFORMATION: Synthetic nucleotide

<400> SEQUENCE: 43
atccgaattc aggtggaggt tcgtgtttgt gggcagatgt tagtgagctg      50

<210> SEQ ID NO 44
<211> LENGTH: 53
<212> TYPE: DNA
<213> ORGANISM: Artificial
<220> FEATURE:
<223> OTHER INFORMATION: Synthetic nucleotide

<400> SEQUENCE: 44
atccgaattc aggtggaggt tcgtgtttgt ggggtgcagt tagtgagctg gat  53

<210> SEQ ID NO 45
<211> LENGTH: 56
<212> TYPE: DNA
<213> ORGANISM: Artificial
<220> FEATURE:
<223> OTHER INFORMATION: Synthetic nucleotide

<400> SEQUENCE: 45
atccgaattc aggtggaggt tcgtgtttgt ggggtgatgc aagtgagctg gatttt  56

<210> SEQ ID NO 46
<211> LENGTH: 56
<212> TYPE: DNA
<213> ORGANISM: Artificial
<220> FEATURE:
<223> OTHER INFORMATION: Synthetic nucleotide

<400> SEQUENCE: 46
tcggccgcaa gcttttagct acacagaaaa tccagctctg caacatcacc ccacaa  56

<210> SEQ ID NO 47
<211> LENGTH: 53
<212> TYPE: DNA
<213> ORGANISM: Artificial
<220> FEATURE:
<223> OTHER INFORMATION: Synthetic nucleotide

<400> SEQUENCE: 47

```
tcggccgcaa gcttttagct acacagaaaa tccagtgcac taacatcacc cca        53
```

<210> SEQ ID NO 48
<211> LENGTH: 50
<212> TYPE: DNA
<213> ORGANISM: Artificial
<220> FEATURE:
<223> OTHER INFORMATION: Synthetic nucleotide

<400> SEQUENCE: 48

```
tcggccgcaa gcttttagct acacagaaaa tctgcctcac taacatcacc            50
```

<210> SEQ ID NO 49
<211> LENGTH: 47
<212> TYPE: DNA
<213> ORGANISM: Artificial
<220> FEATURE:
<223> OTHER INFORMATION: Synthetic nucleotide

<400> SEQUENCE: 49

```
tcggccgcaa gcttttagct acacagaaat gccagctcac taacatc               47
```

<210> SEQ ID NO 50
<211> LENGTH: 44
<212> TYPE: DNA
<213> ORGANISM: Artificial
<220> FEATURE:
<223> OTHER INFORMATION: Synthetic nucleotide

<400> SEQUENCE: 50

```
tcggccgcaa gcttttagct acacagtgca tccagctcac taac                  44
```

<210> SEQ ID NO 51
<211> LENGTH: 41
<212> TYPE: DNA
<213> ORGANISM: Artificial
<220> FEATURE:
<223> OTHER INFORMATION: Synthetic nucleotide

<400> SEQUENCE: 51

```
tcggccgcaa gcttttagct acatgcaaaa tccagctcac t                     41
```

<210> SEQ ID NO 52
<211> LENGTH: 38
<212> TYPE: DNA
<213> ORGANISM: Artificial
<220> FEATURE:
<223> OTHER INFORMATION: Synthetic nucleotide

<400> SEQUENCE: 52

```
tcggccgcaa gcttttagct tgccagaaaa tccagctc                         38
```

<210> SEQ ID NO 53
<211> LENGTH: 35
<212> TYPE: DNA
<213> ORGANISM: Artificial
<220> FEATURE:
<223> OTHER INFORMATION: Synthetic nucleotide

<400> SEQUENCE: 53

```
tcggccgcaa gcttttatgc acacagaaaa tccag                            35
```

<210> SEQ ID NO 54
<211> LENGTH: 79
<212> TYPE: DNA

```
<213> ORGANISM: Artificial
<220> FEATURE:
<223> OTHER INFORMATION: Synthetic peptide
<220> FEATURE:
<221> NAME/KEY: misc_feature
<222> LOCATION: (24)..(56)
<223> OTHER INFORMATION: n is a, c, g, or t

<400> SEQUENCE: 54
cgaattcagg tggaggttcg tgtnnnnnnn nnnnnnnnnn nnnnnnnnnn nnnnnntgta      60
gctaaaagct tgcggccga                                                   79

<210> SEQ ID NO 55
<211> LENGTH: 79
<212> TYPE: DNA
<213> ORGANISM: Artificial
<220> FEATURE:
<223> OTHER INFORMATION: Synthetic peptide
<220> FEATURE:
<221> NAME/KEY: misc_feature
<222> LOCATION: (24)..(56)
<223> OTHER INFORMATION: n is a, c, g, or t

<400> SEQUENCE: 55
cgaattcagg tggaggttcg tgtnnnnnnn nnnnnnnnnn nnnnnnnnnn nnnnnntgta      60
gctaaaagct tgcggccga                                                   79
```